(12) United States Patent
Henderson et al.

(10) Patent No.: US 9,017,953 B2
(45) Date of Patent: Apr. 28, 2015

(54) BIOMARKER AND THERAPEUTIC FOR URINARY TRACT INFECTION

(71) Applicant: The Washington University, St. Louis, MO (US)

(72) Inventors: Jeffrey P. Henderson, St. Louis, MO (US); Chia Hung, Fenton, MO (US); Kaveri Chaturvedi, Moline, IL (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 13/897,869

(22) Filed: May 20, 2013

(65) Prior Publication Data
US 2013/0309687 A1 Nov. 21, 2013

Related U.S. Application Data

(60) Provisional application No. 61/648,939, filed on May 18, 2012.

(51) Int. Cl.
| | | |
|---|---|---|
| A61K 33/34 | (2006.01) | |
| A61K 8/64 | (2006.01) | |
| C07K 1/14 | (2006.01) | |
| C12Q 1/10 | (2006.01) | |

(52) U.S. Cl.
CPC .............. *C12Q 1/10* (2013.01); *G01N 2800/52* (2013.01)

(58) Field of Classification Search
CPC ... A61K 33/34; A61K 2300/00; A61K 31/30; A61K 8/64; C07K 1/22; C07K 1/14; C07K 1/00; C07K 2/00; C12N 2303/02; C12N 2320/10; C12Q 2527/125
USPC .............. 424/94.1, 630, 604; 435/7.1, 234, 4; 436/86, 174, 73, 80; 514/499
See application file for complete search history.

(56) References Cited

U.S. PATENT DOCUMENTS

2006/0269564 A1* 11/2006 Emery et al. ................ 424/190.1

OTHER PUBLICATIONS

Bultreys et al. 2006 (Yersiniabactin Production by *Pseudomonas syringae* and *Escherichia coli* and Description of a Second Yersiniabactin Locus Evolutionary Group; Appl. Environ. Microbiol. 72(6):3814-3825).*
Chaturvedi et al. 2012 (The siderophore yersiniabactin binds copper to protect pathogens during infection; Nat. Chem. Biol. 8(8):731-736).*
Chaturvedi et al. 2014 (Pathogenic adaptations to host-derived antibacterial copper; Frontiers in Cellular and Infection Microbiology 4(3): 1-12).*
Henderson et al. 2009 (Quantitative Metabolomics Reveals an Epigenetic Blueprint for Iron Acquisition in Uropathogenic *Escherichia coli*; PLoS Pathogens 5(2):1-11).*
Henderson et al. 2012 (An Interdisciplinary Approach Reveals a New Function for Yersiniabactin, a Uropathogen Virulence Factor; Journal of Women's Health 21: 992).*
Bautzova et al., "Multiparticulate systems containing 5-aminosalicylic acid for the treatment of inflammatory bowel disease", Drug Development and Industrial Pharmacy, 2011, pp. 1100-1109, vol. 37, No. 9.
Bertolini et al., "A New Rational Hypothesis for the Pharmacophore of the Active Metabolite of Leflunomide, a Potent Immunosuppressive Drug", Journal of Medicinal Chemistry, 1997, pp. 2011-2016, vol. 40, No. 13.
Bodor, "Novel Approaches to the Design of Safer Drugs: Soft Drugs and Site-Specific Chemical Delivery Systems", Advances in Drug Research, 1984, pp. 255-331, vol. 13.
Henderson et al., "Quantitative Metabolomics Reveals an Epigenetic Blueprint for Iron Acquisition in Uropathogenic *Escherichia coli*", PLoS Pathogens, 2009, e1000305, 11 pgs., vol. 5, No. 2.
Lee et al., "New Synthetic Cluster Ligands for Galactose/N-Acetylgalactosamine-Specific Lectin of Mammalian Liver", Biochemistry, 1984, pp. 4255-4261, vol. 23, No. 18.
Lichtenstein et al. "Review article: 5-aminosalicylate formulations for the treatment of ulcerative colitis—methods of comparing release rates and delivery of 5-aminosalicylate to the colonic mucosa", Alimentary Pharmacology & Therapeutics, 2008, pp. 663-673, vol. 28.
Marschall et al., "Both Host and Pathogen Factors Predispose to *Escherichia coli* Urinary-Source Bacteremia in Hospitalized Patients", Clinical Infectious Diseases, 2012, pp. 1692-1698, vol. 54, No. 12.
Nagachar et al., "Knocking out salicylate biosynthesis genes in *Mycobacterium smegmatis* induces hypersensitivity to p-aminosalicylate (PAS)", FEMS Microbiol Lett., 2010, pp. 193-199, vol. 311, No. 2.
Ratledge et al., "Inhibition of Mycobactin Formation in *Mycobacterium smegmatis* by p-Aminosalicylate. A New Proposal for the Mode of Action of p-Aminosalicylate", American Review of Respiratory Disease, 1972, pp. 774-776, vol. 106, No. 5.
Roberts et al., "Total (Bio)Synthesis: Strategies of Nature and of Chemists", Top Curr Chem., 2010, pp. 149-203, vol. 297.
Shan et al., "Prodrug Strategies Based on Intramolecular Cyclization Reactions", Journal of Pharmaceutical Sciences, 1997, pp. 765-767, vol. 86, No. 7.
Simplicio et al., "Prodrugs for Amines", Molecules, 2008, pp. 519-547, vol. 13.
Snyder et al., "Transcriptome of Uropathogenic *Escherichia coli* during Urinary Tract Infection", Infection and Immunity, 2004, pp. 6373-6381, vol. 72, No. 11.
Yue et al., "Toleration and Absorption of Sodium Para-Aminosalicylate and Para-Aminosalicylic Acid (Neopasalate), Comparison with Other Forms of Para-Aminosalicylic Acid," Diseases of the Chest, 1966, pp. 165-174, vol. 49, No. 2.

* cited by examiner

*Primary Examiner* — J Hines
*Assistant Examiner* — Mary Lyons
(74) *Attorney, Agent, or Firm* — Polsinelli PC

(57) ABSTRACT

The present invention encompasses methods and compositions for detecting pathogenic bacteria. Additionally, the present invention encompasses methods and compositions for catalyzing the dismutation of superoxide radicals.

8 Claims, 33 Drawing Sheets
(4 of 33 Drawing Sheet(s) Filed in Color)

US 9,017,953 B2

BIOMARKER AND THERAPEUTIC FOR URINARY TRACT INFECTION

CROSS REFERENCE TO RELATED APPLICATIONS

This application claims priority to U.S. provisional application No. 61/648,939, filed May 18, 2012, which is hereby incorporated by reference in its entirety.

GOVERNMENTAL RIGHTS

This invention was made with government support under NIH grant numbers K12 HD001459-09, AI 07172-24, P30 HL101263-01, P50 DK64540, U01 DK082315, and UL1 RR024992. The government has certain rights in the invention.

FIELD OF THE INVENTION

The present invention encompasses methods and compositions for detecting pathogenic bacteria. Additionally, the present invention encompasses methods and compositions for catalyzing the dismutation of superoxide radicals.

BACKGROUND OF THE INVENTION

Urinary tract infection (UTI) caused by uropathogenic *Escherichia coli* (UPEC) is one of the most common infectious diseases in women. The morbidity and economic impact are enormous, with over $2.5 billion spent annually on treatment. Further, recurrent infections are a significant problem despite appropriate antibiotic therapy of the index case. The high rates of recurrence, and the large numbers of women that end up in urology clinics due to their chronic recurrent UTIs highlights the need for a better understanding of the pathogenic mechanisms involved in this disease and the development of new and better therapies. The high frequency of same-strain recurrences supports the notion that a UPEC quiescent intracellular reservoir (QIR) can exist in the affected individual, and persist even after antibiotic therapy and urine cultures become sterile. Current diagnostic schemes for these bacteria are based on culture and do not distinguish between strains with high or low virulence potential.

Therefore, there is a need for an effective biomarker for urinary tract infections that avoids false negative results that occur when culture-based methods are applied during antibiotic therapy or when culture or nucleic acid-based methods are applied to patients in which bacteria are not actively shed into sampled fluids. In addition, there is a need for effective treatments that can cure urinary tract infections and prevent infection by quiescent intracellular reservoirs of pathogenic bacteria that are the source of so many recurrent urinary tract infections.

SUMMARY OF THE INVENTION

One aspect of the present invention encompasses a method for detecting the presence of pathogenic bacteria in a subject. The method comprises the steps of: a) obtaining a sample from the subject, b) analyzing the sample, in vitro, for the presence or absence of cupric yersiniabactin, and c) identifying the presence of pathogenic bacteria in the subject when cupric yersiniabactin is present in the sample.

Another aspect of the present invention encompasses a method for determining whether a subject would benefit from a compound that inhibits yersiniabactin. The method comprises a) obtaining a sample from the subject, b) analyzing the sample, in vitro, for the presence or absence of cupric yersiniabactin, and c) identifying the subject as a subject that would benefit from a compound that inhibits yersiniabactin when cupric yersiniabactin is present in the sample.

Yet another aspect of the present invention encompasses a method for catalyzing the dismutation of a superoxide radical. The method comprises contacting a superoxide radical with yersiniabactin complexed with a redox-active metal.

Other aspects and iterations of the invention are described in more detail below.

BRIEF DESCRIPTION OF THE FIGURES

The patent or application file contains at least one drawing executed in color. Copies of this patent or patent application publication with color drawing(s) will be provided by the Office upon request and payment of the necessary fee.

bladder and (B) urine extracts from infected, but not uninfected, animals. (C) In the infected urine samples, the median Cu(II)-Ybt:Fe(III)-Ybt ratio is 15.3, indicating that yersiniabactin preferentially binds copper (II) in vivo.

Figure 5:
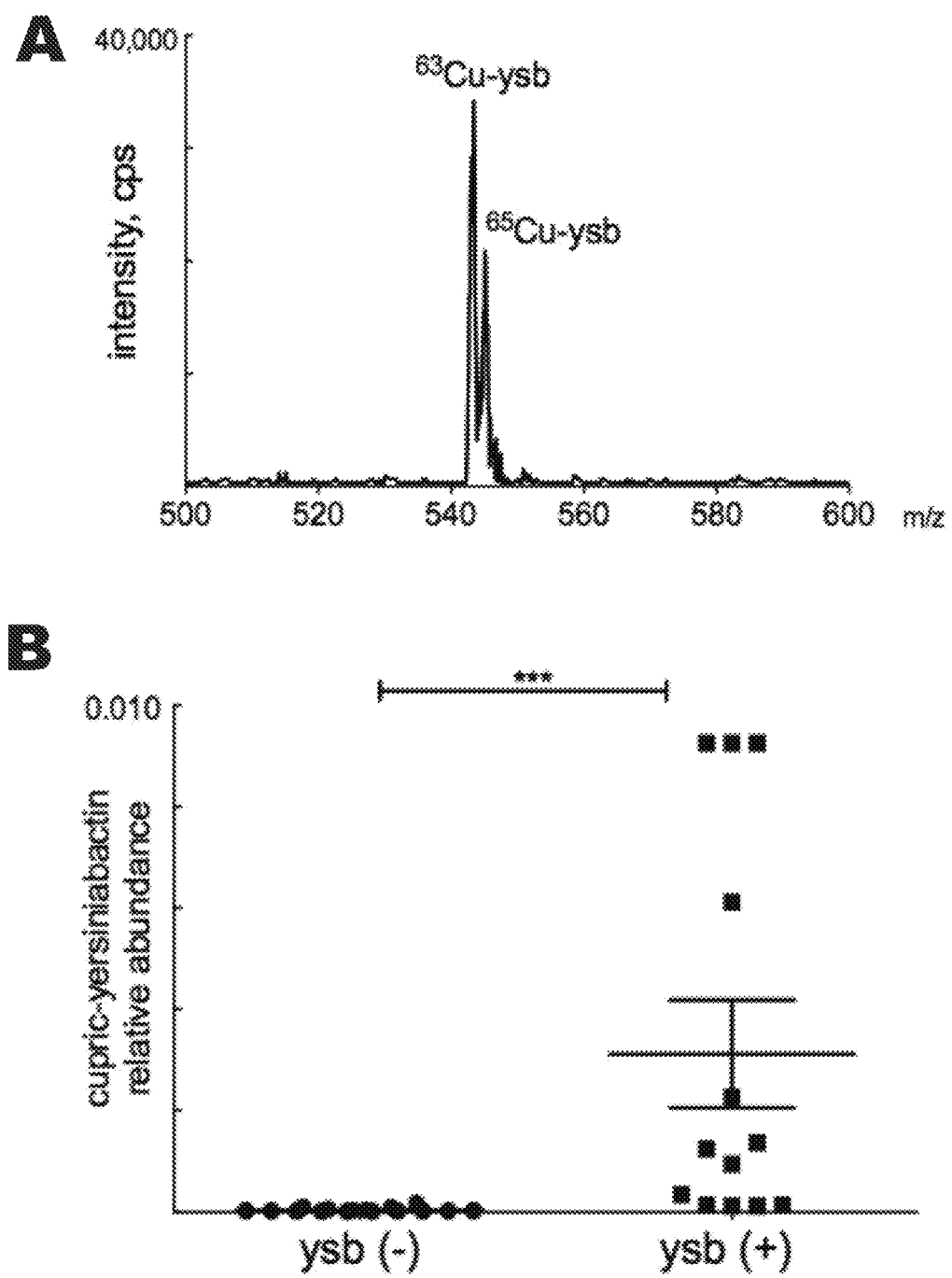

FIG. 5 Cupric-yersiniabactin is produced in cystitis patients infected with yersiniabactin-producing strains. (A) A scanning constant neutral loss spectrum reveals the spectrum for Cu(II)-Ybt at its expected retention time. The expected copper isotope peaks at m/z 543 for $^{63}$Cu and m/z 545 for 65Cu peak are indicated. (B) Urinary Cu(II)-Ybt was detected in 13 of 15 patients infected with a yersiniabactin-expressing pathogen and in none of the patients with yersiniabactin non-expressors. Cu(II)-Ybt levels are reported as a fraction of the corresponding $^{13}$C internal standard peak height. (C) In urine samples with detectable yersiniabactin complexes, the median Cu(II)-Ybt (m/z 543) to Fe(III)-Ybt (m/z 535) ratio is 2.941, indicating preferential in vivo copper (II) binding.

Figure 6:
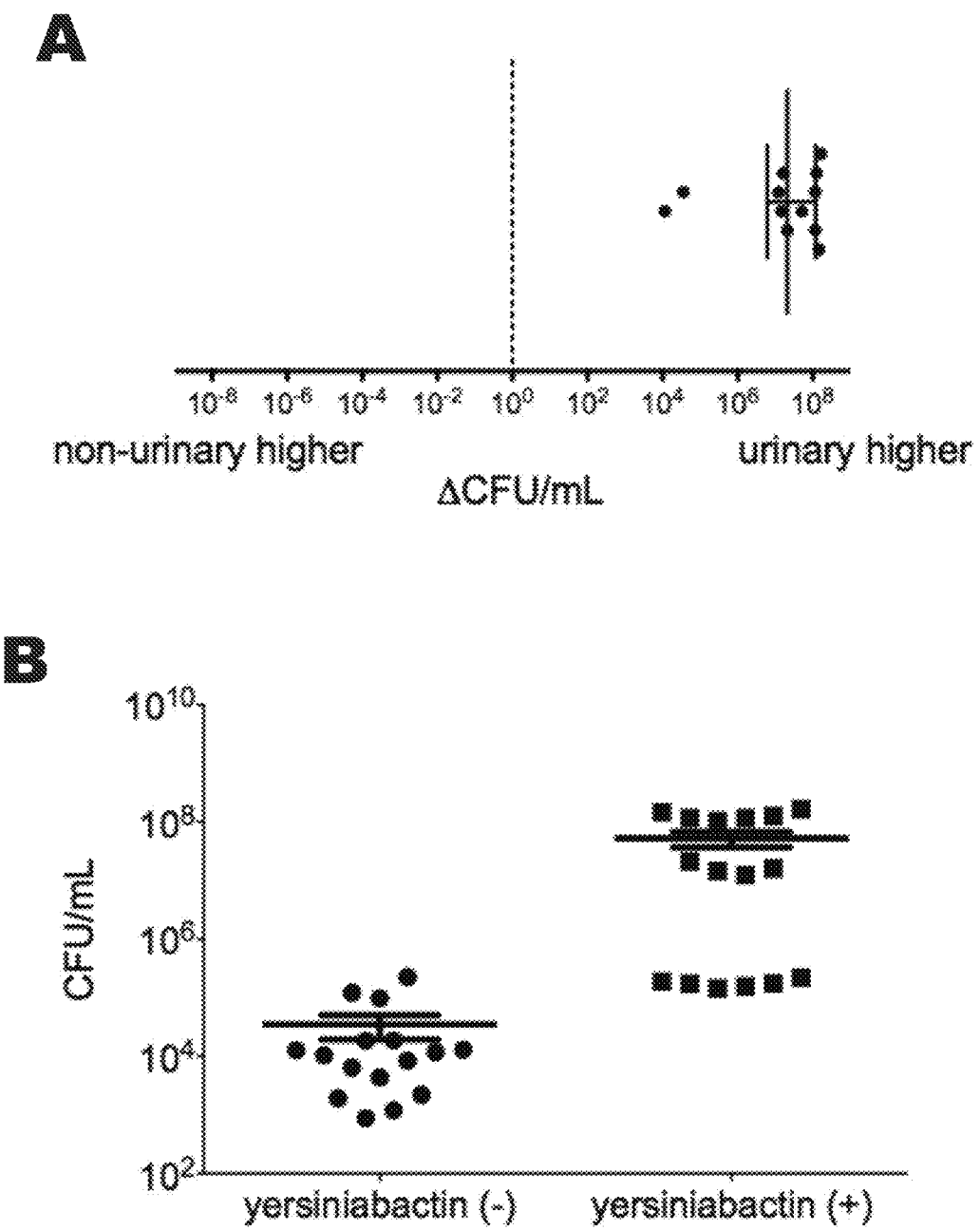

FIG. 6 Yersiniabactin promotes E. coli growth in copper-toxic conditions. Urinary and non-urinary E. coli isolates from a UTI patient population were cultured in the presence of 10 M copper (II) sulfate for 18 hours. Growth was determined and expressed as total CFU/mL. (A) Urinary strains demonstrate greater resistance to copper toxicity that coexisting rectal strains. For each patient, the number of viable bacteria from the non-urinary source was subtracted from the number of viable coincident urinary strains to yield a difference. In the four patients from whom multiple coincident urinary and non-urinary strains were recovered, the mean difference in siderophore production is reported. The median value of these differences was $2.11 \times 10^7$ CFU/mL, with a range of $-5.4 \times 10^3$ to $1.66 \times 10^8$. (B) Yersiniabactin-expressors were more resistant to copper toxicity than non-expressors (p<0.0013). These results were confirmed in three independent experiments. (C) Yersiniabactin-expressor (UTI89) and non-expressor (UTI89ΔybtS) cultures treated with 0-25 M copper (II) sulfate revealed an average of ten-fold survival advantage for the yersiniabactin expressor (p=0.0044, t-test). (D) Purified apo-yersiniabactin or Cu(II)-Ybt was added in 1.5-fold molar excess over 10 M copper (II) sulfate to yersiniabactin-deficient (UTI89ΔybtS) culture. Samples containing copper alone demonstrated a >3 log CFU/mL decrease in viability. Apo-yersiniabactin (apo-Ybt) addition restores growth to untreated wild type levels (p=ns). This cytoprotective effect is unique to apo-yersiniabactin, and is not observed upon addition of pre-formed Cu(II)-Ybt. These results were confirmed in three independent experiments.

Figure 7A:
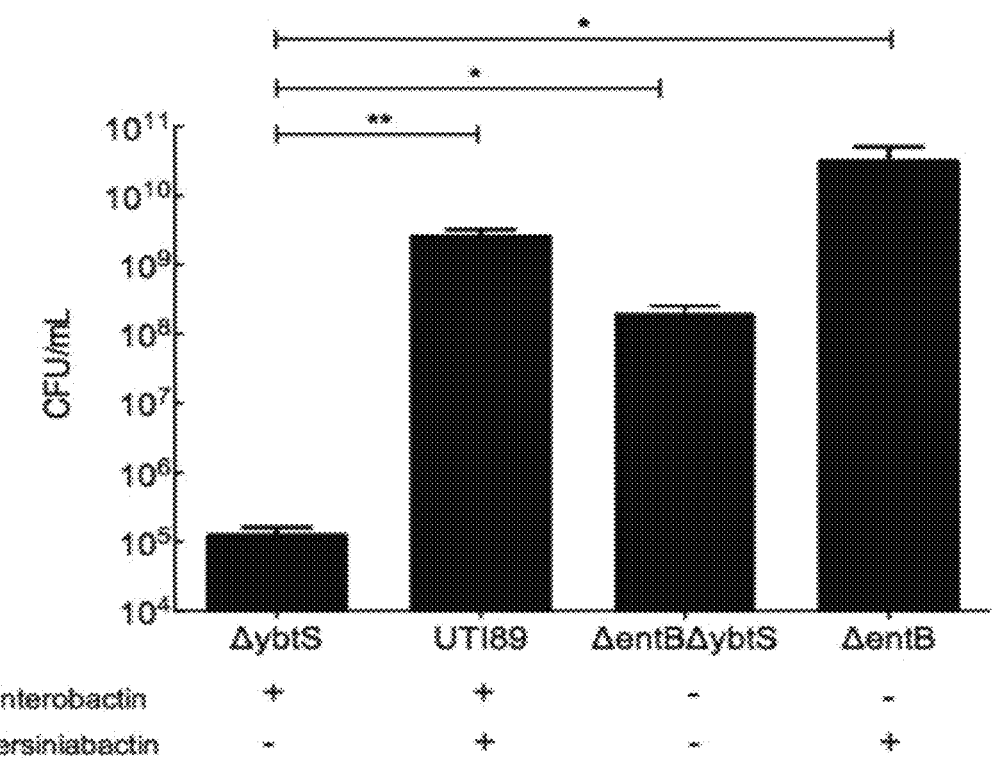
Figure 7B:
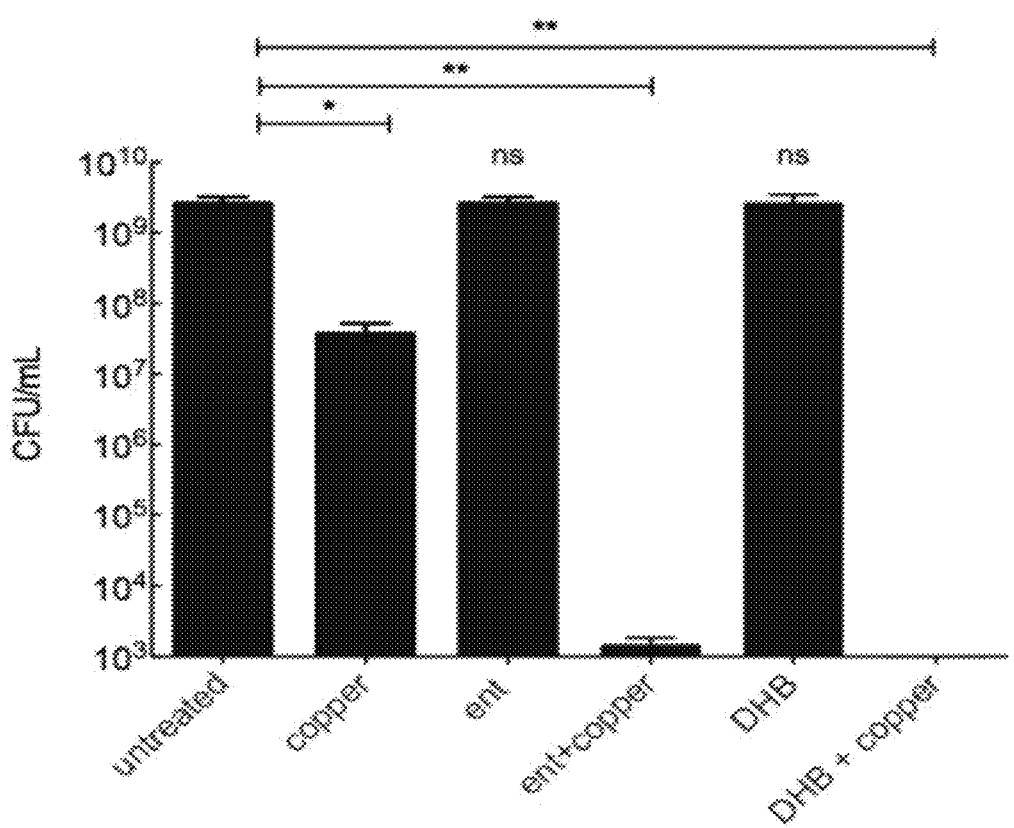
Figure 7:
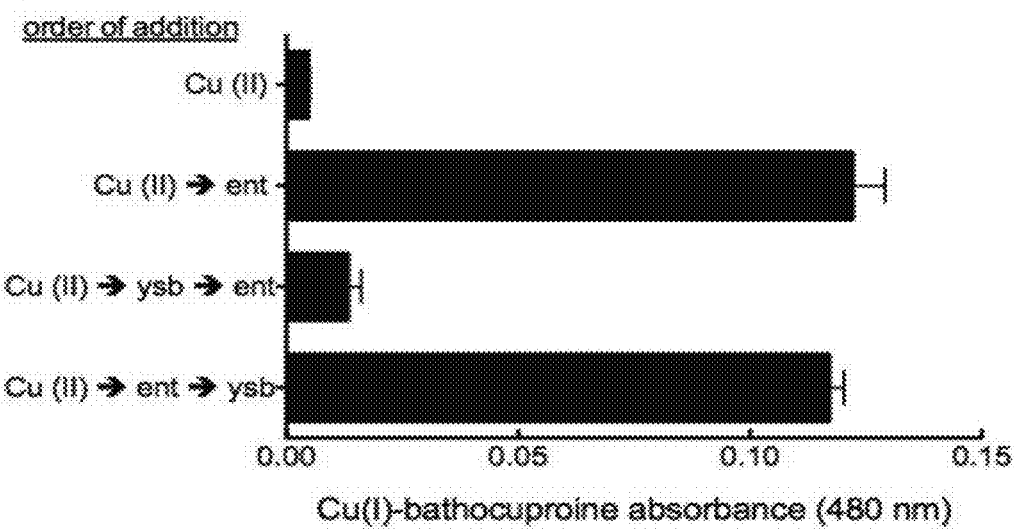
Figure 7:
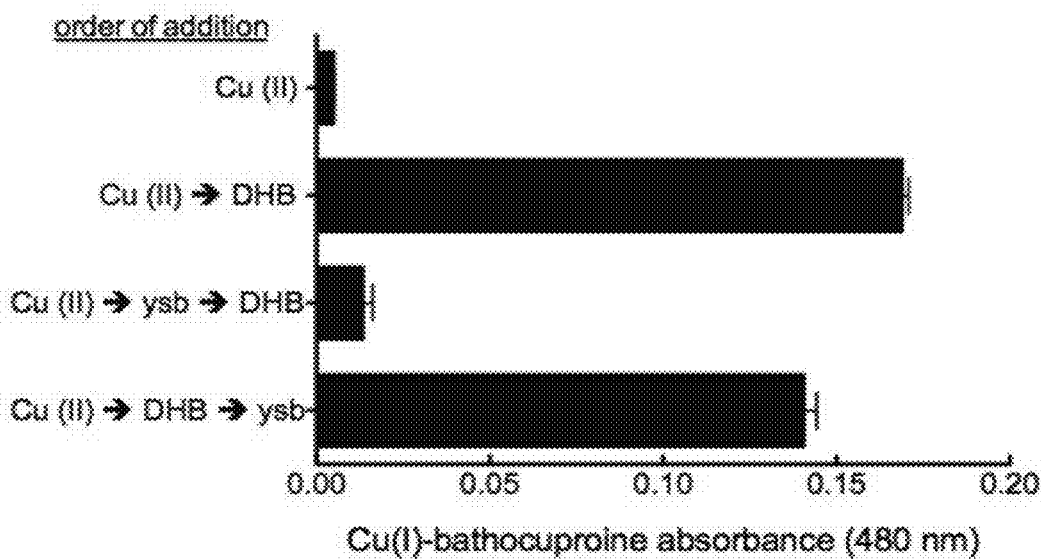

FIG. 7 Catecholate siderophores and yersiniabactin exert opposing effects on copper cytotoxicity. (A) Growth of wild type (UTI89), yersiniabactin (ΔybtS), catecholate siderophore (ΔentB), or total siderophore (ΔentBΔybtS) expression mutants in the presence of copper was determined. Results were consistent with copper-dependent cytoprotective effect for yersiniabactin and cytotoxic effect for catecholate siderophores. (B) Exogenous addition of 20 μM of the siderophore enterobactin, or its catecholate moiety 2,3-dihydroxybenzoate (DHB) enhances copper (II) sulfate toxicity in UTI89. (C, D) Apo-yersiniabactin prevents catechol-dependent reduction of copper (II) sulfate to copper (I) in an order-of-addition dependent manner. The complete reaction system consisted of 17.5 M copper(II) sulfate, either 20 μM enterobactin (ent) or its catecholate moiety 2,3-dihydroxybenzoic acid (DHB), 25 M apo-yersiniabactin (Ybt), and 25 μM of the copper(I) indicator bathocuproine sulfonate. Reagents were added in the order indicated and Cu(I)-bathocuproine absorbance was determined 30 min after addition of the last reagent. Results were confirmed in three independent experiments.

Figure 8:
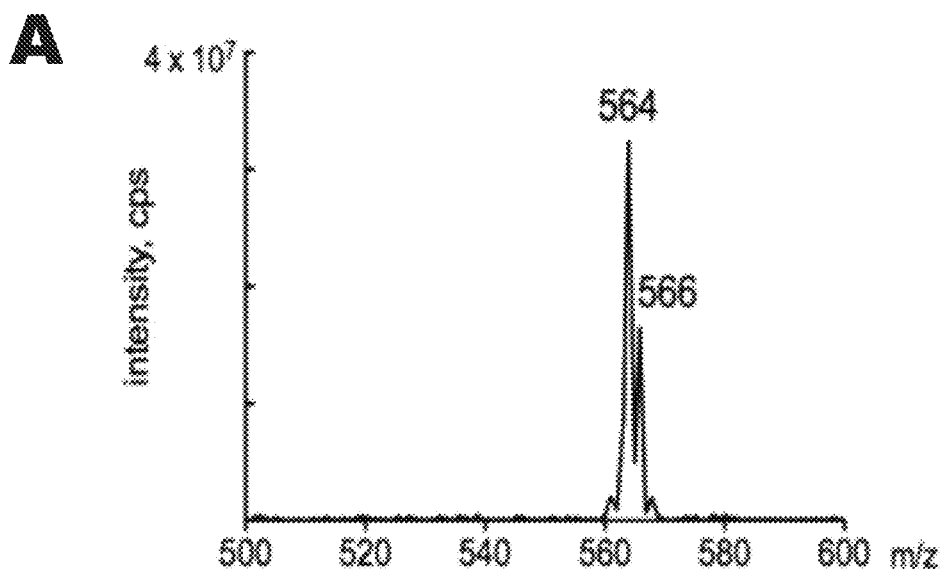
Figure 8:
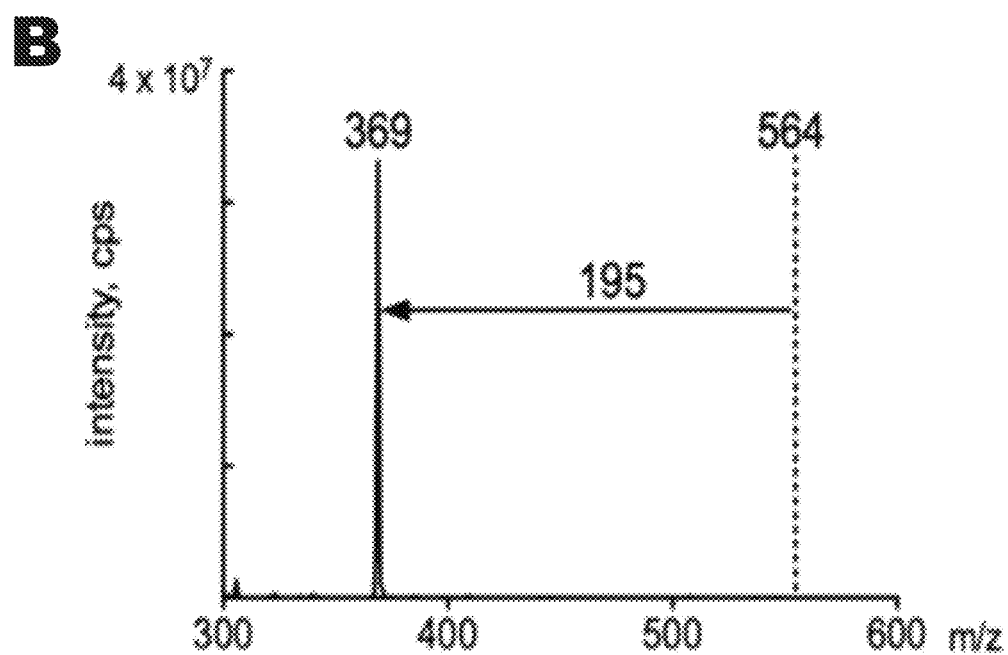

FIG. 8 Structural confirmation of copper (II)-yersiniabactin complexes by isotope labeling. $^{13}$C-labeled internal standard was treated with 3.0 mM copper (II) sulfate and purified over a preparative C18 column. (A) Full scan positive ion ESI spectrum at the Cu(II)-Ybt retention time reveals an [M+H]$^+$ peak at m/z 564 and M+2 at m/z 566, consistent with $^{13}$C-substitution of all 21 carbon atoms in yersiniabactin and the copper M+2 isotope. (B) MS/MS of the m/z 564 ion revealed a shifted dominant MS/MS neutral loss of 195 mass units, corresponding to loss of a fragment containing eight carbons.

Figure 9:
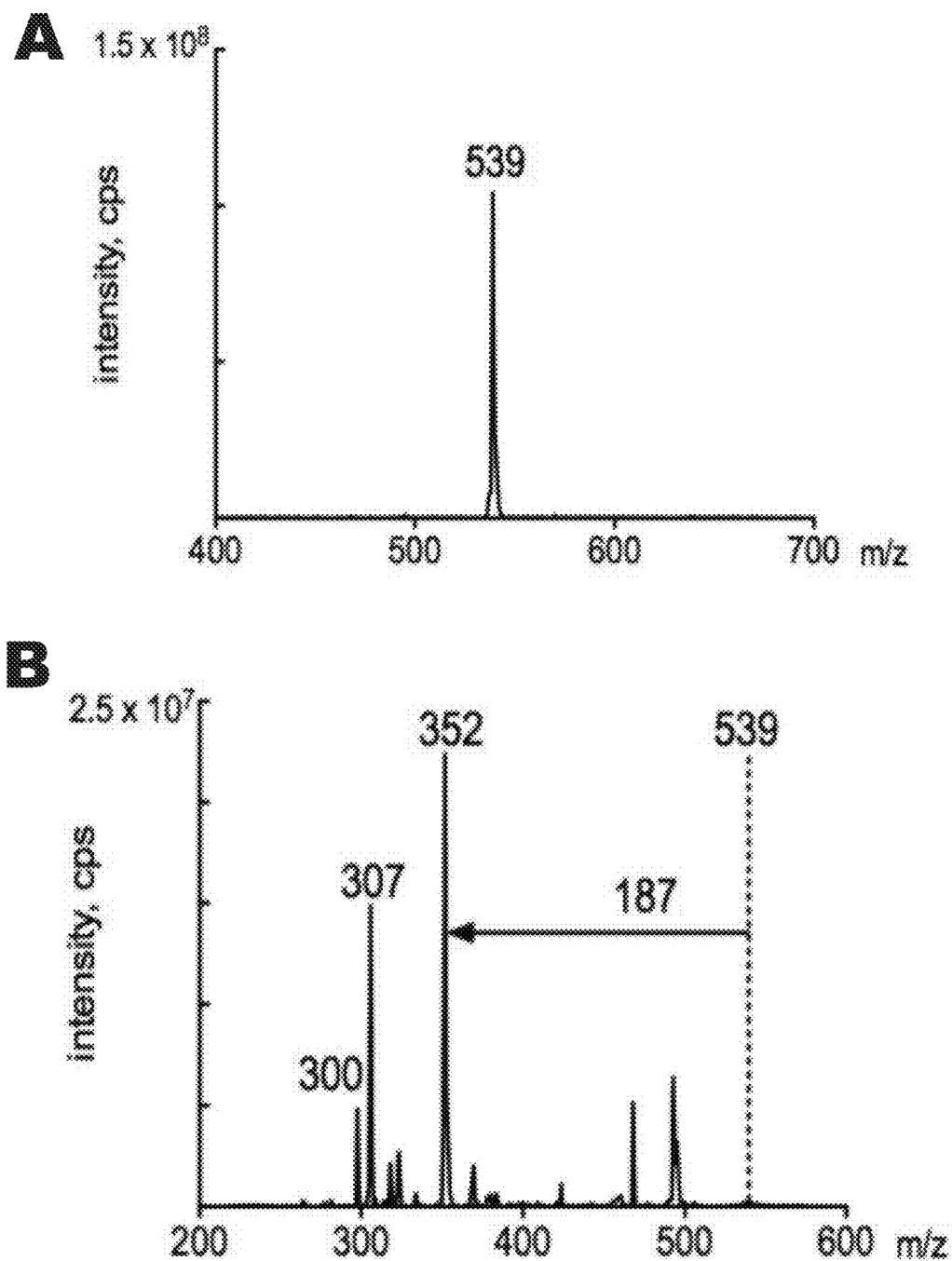

FIG. 9 Preparation of deuterated yersiniabactin. $d_4$-ferric-yersiniabactin was produced by chemically complementing the salicylate synthase-deficient mutant UTI89ΔybtS with 50 μM $d_6$-salicylate during growth in M63 minimal medium containing 0.2% unlabeled glycerol. (A) Full scan positive ion ESI spectrum at the Fe(III)-Ybt retention time reveals an [M+H]+ peak at m/z 539, consistent with introduction of the four nonexchangable deuterons in $d_6$-salicylate. (B) MS/MS of the m/z 539 ion revealed a dominant 187 m/z unit neutral loss, consistent with neutral loss of a fragment from yersiniabactin's unlabeled carboxylic acid terminus.

Figure 10:
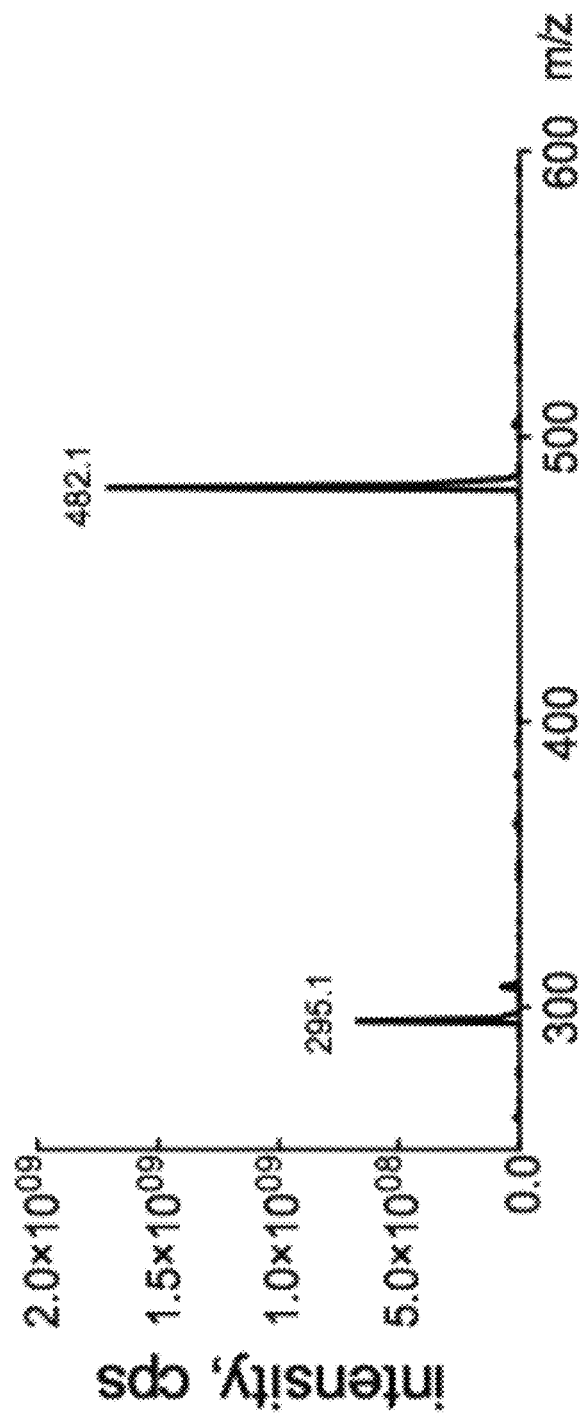

FIG. 10 Mass spectrum of apo-yersiniabactin. Depicted is the positive ESI mass spectrum of a sample from the apo-yersiniabactin preparation used in this study. The predicted [M+H]$^+$ molecular ion at 482 m/z units is evident, along with the [M+H-187]$^+$ source decay fragment at m/z 295.

Figure 11:
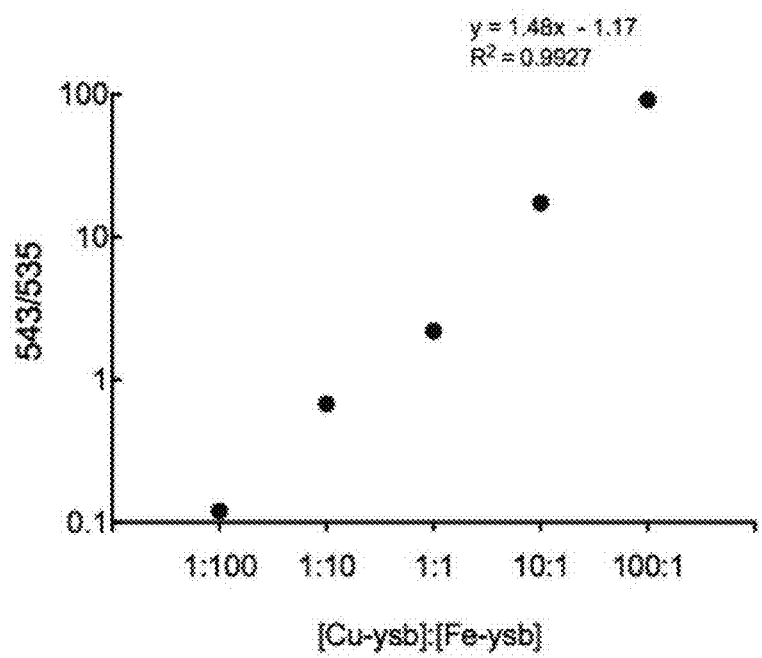
Figure 11:
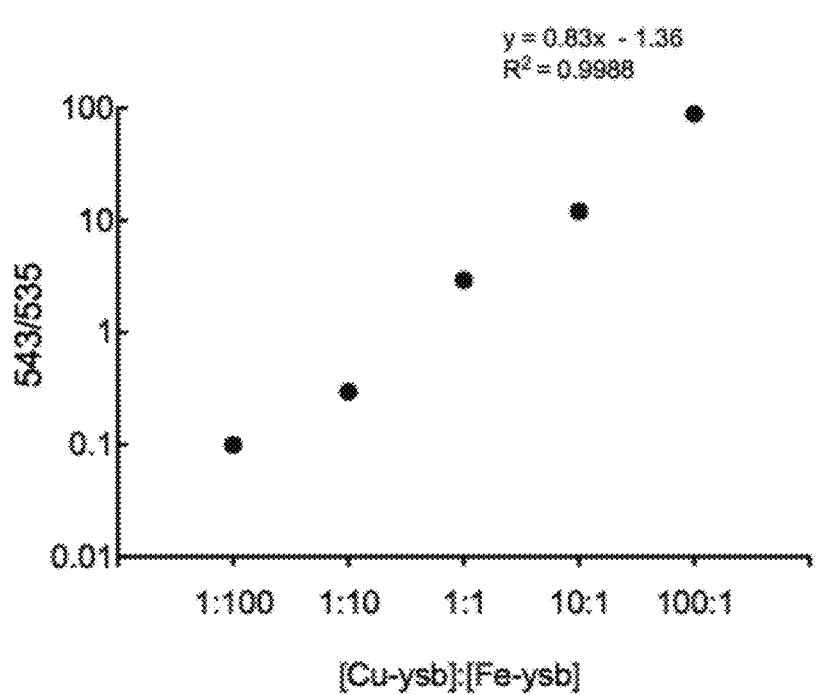

FIG. 11 Calibration curves for the determination of Cu(II)-Ybt to Fe(III)-Ybt molar ratios. Standard curves used for in vitro analysis were performed in phosphate buffered saline (PBS, panel A). Curves used for in vivo analyses were performed in human urine (panel B). The Y axes refer to the LCMS/MS peak area ratios derived from the Cu(II)-Ybt precursor ion at 543 m/z units and the Fe(III)-Ybt precursor ion at 535 m/z units. Both curves exhibited broad linear responses and slopes near unity.

Figure 12:
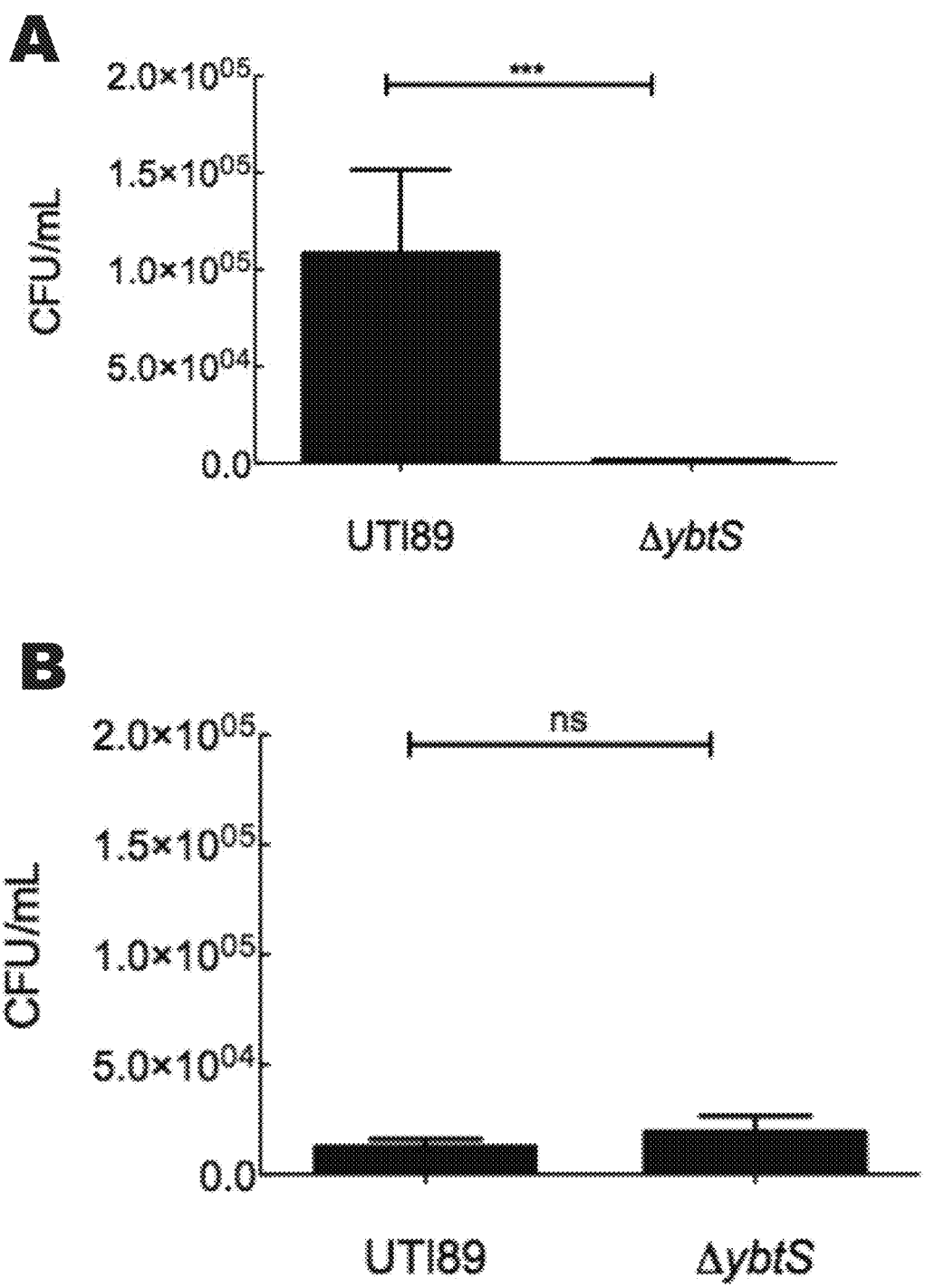

FIG. 12 Yersiniabactin is a determinant of UTI89 survival within copper-treated RAW264.7 macrophages. RAW264.7 macrophages were infected with UTI89 or the ybtS deficient mutant following treatment (A) with or (B) without 20 μm copper sulfate. After removal of extracellular bacteria, bacterial survival was measured following incubations for 1 hour at 37° C. and expressed as a percentage of initial internalized E. coli (mean±S.D.; n=3; p<0.0032, Student's t test). UTI89 is significantly (p=0.001) more viable than the ybtS deficient mutant only in macrophages that have been treated with copper. This indicates that the expression of yersiniabactin selectively attenuates the copper-dependent bactericidal activity of macrophages. These experiments were conducted in triplicate.

FIG. 13 Superoxide dismutase activity associated with UTI89 fractions. Copper treated and untreated culture supernatants of UTI89, ΔybtS and ΔentB were subjected to preparative chromatography, and the resulting methanolic fractions were tested for superoxide dismutase (SOD) activity. (A) SOD activity is observed in the 80% methanolic extracts of copper treated UTI89 and ΔentB, but not the ΔybtS culture supernatants. This is the fraction associated with yersiniabactin purification. (B) SOD activity is not observed in UTI89, ΔentB or ΔybtS culture supernatants, indicating that this enzymatic activity requires the interaction of copper and yersiniabactin. The data are presented as means±SD of three independent experiments.

Figure 14:
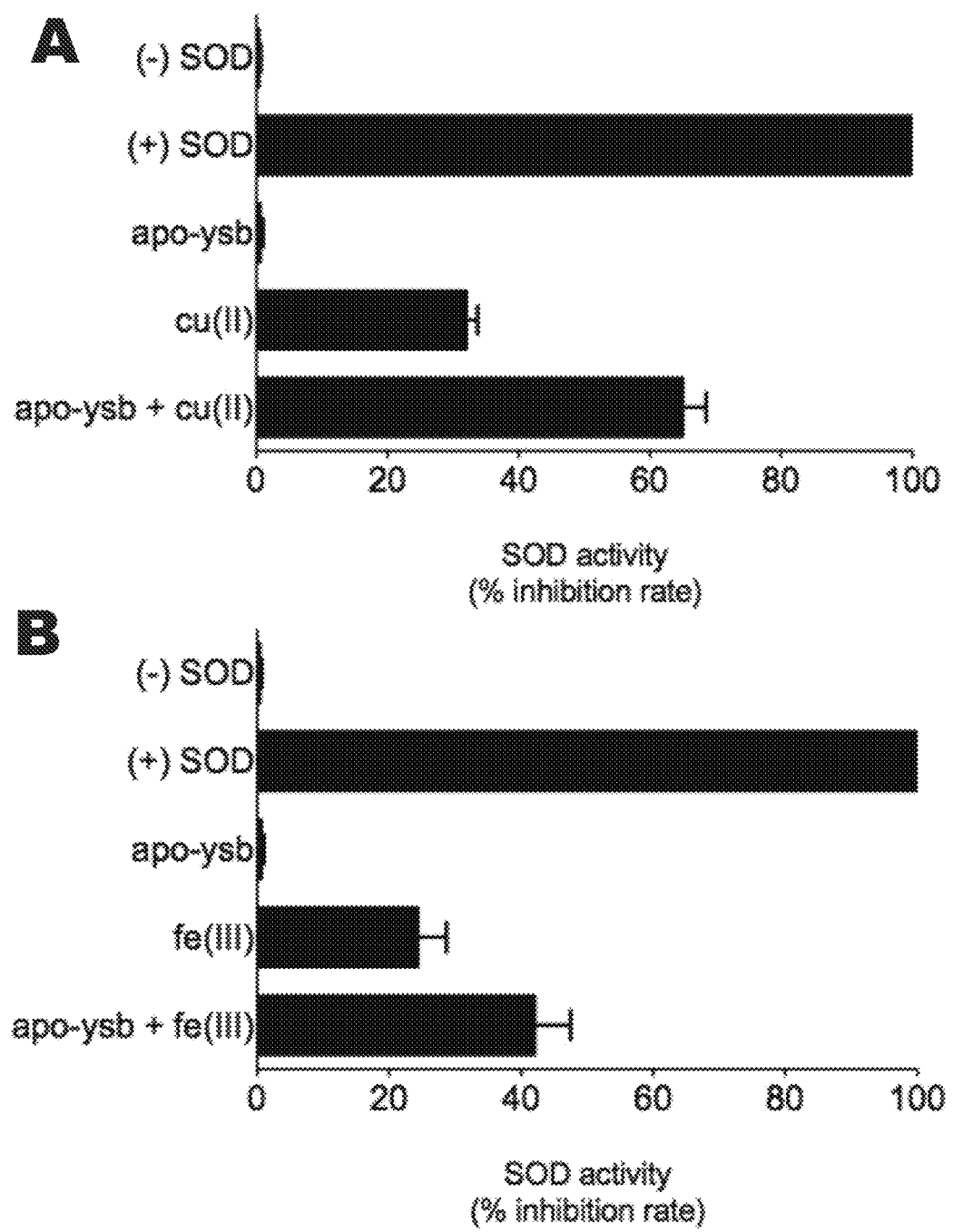
Figure 14:
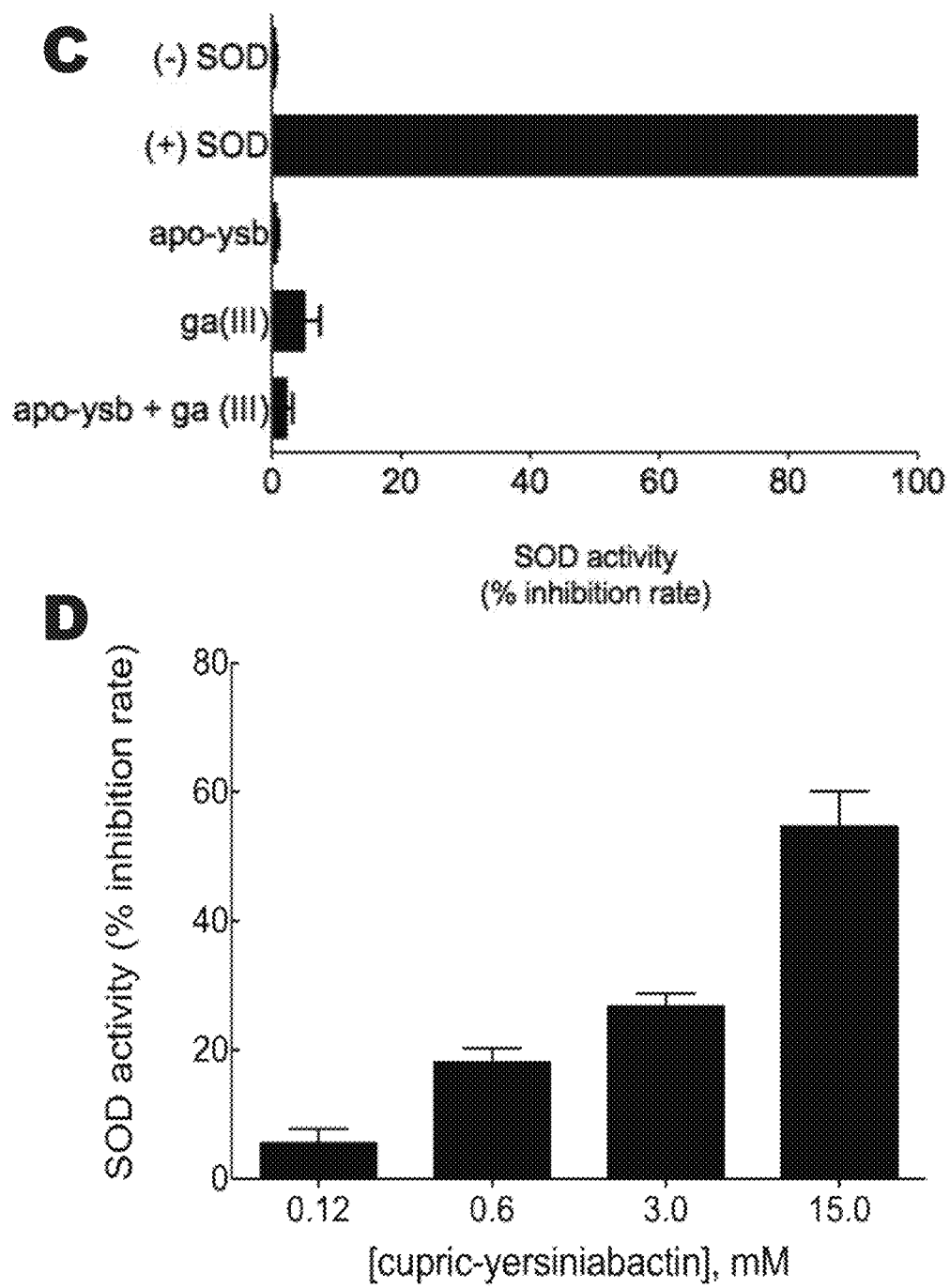

FIG. 14 Cupric yersiniabactin is a superoxide dismutase mimic. Apo- and metal-complexes of yersinabactin were assessed for SOD activity using a WST-formazan based colorimetric assay. Results are reported as a normalized percentage compared to positive controls treated with bovine superoxide dismutase. (A) Percentage inhibition rate of 63.12% is associated with copper (II)-yersiniabactin, but not with apo-yersiniabactin alone. (B) 41.4% inhibition rate is observed with ferric complexes of yersiniabactin. (C) While SOD activity is observed in cupric and ferric complexes of yersiniabactin, this activity is abolished in redox inert gallium complexes. SOD activity is dependent on the redox state of the metal bound to yersiniabactin. (D) A dose-response relationship is observed in the SOD activity associated with purified copper (II)-yersiniabactin complexes. The data are presented as means±SD of five independent experiments.

Figure 15:
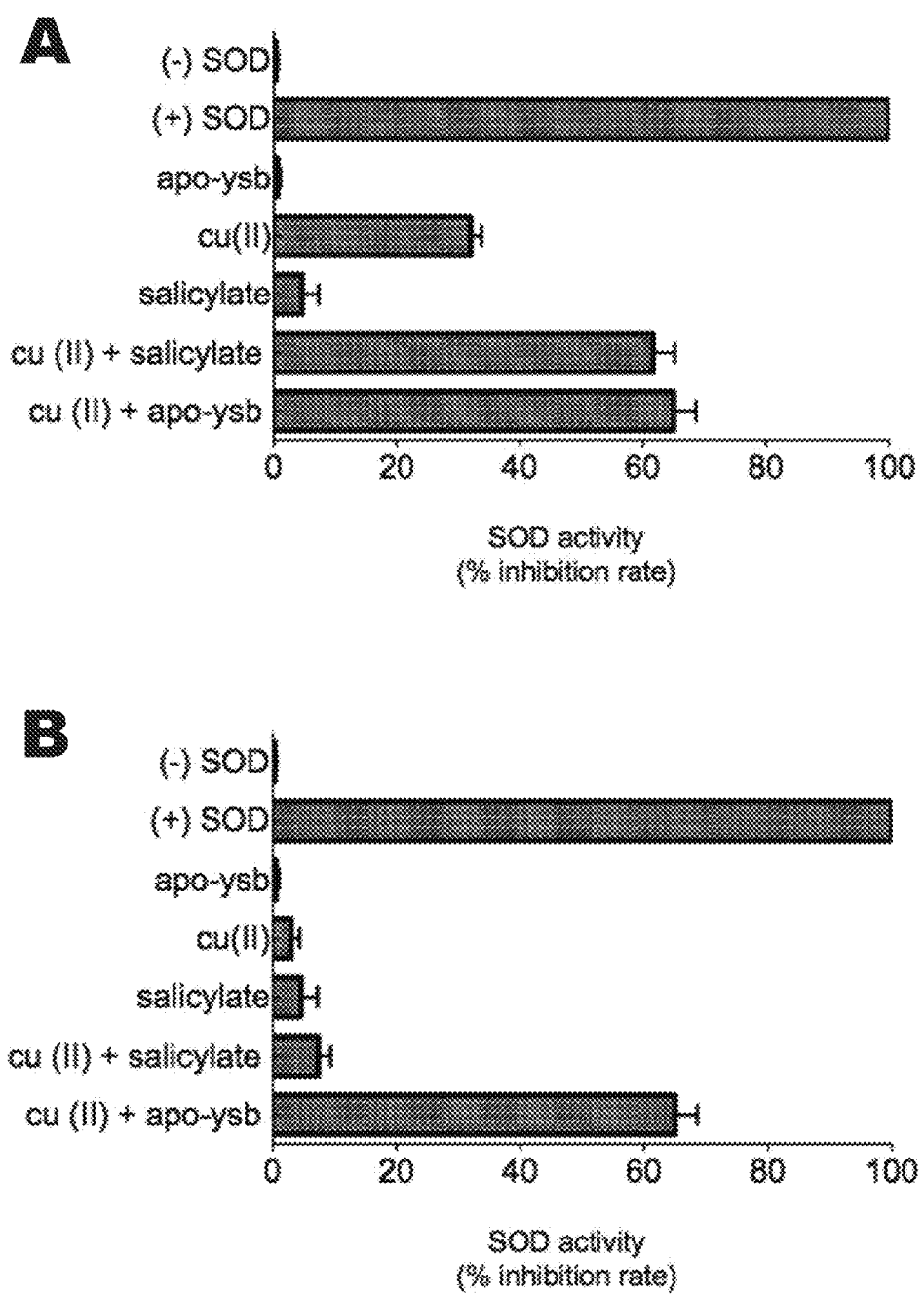

FIG. 15 SOD activity of cupric-yersiniabactin is selectively retained in the presence of protein. (A) The superoxide-dismuting activity of both copper (II) complexes with yersiniabactin and with saliyclate, the synthetic precursor of this siderophore, were determined. The percentage inhition rate associate with copper (II)-salicylate complexes is 61.6%, compared to 65% for copper (II)-yersiniabactin complexes. (B) The superoxide dismutase activity of these complexes was tested in the presence of 1.0 mg/mL bovine serum albumin (BSA) to determine whether this enzymatic activity is retained in a physiologic environment with high concentration of protein. The superoxide dismutase activity associated with copper (II)-salicylate complexes is quenched in the presence of BSA, while this activity is retained in the copper (II) yersiniabactin complexes. This gives a chemical rationale for the complex synthesis of yersiniabactin, instead of relying on a simpler precursor for similar enzymatic activity.

Figure 16:
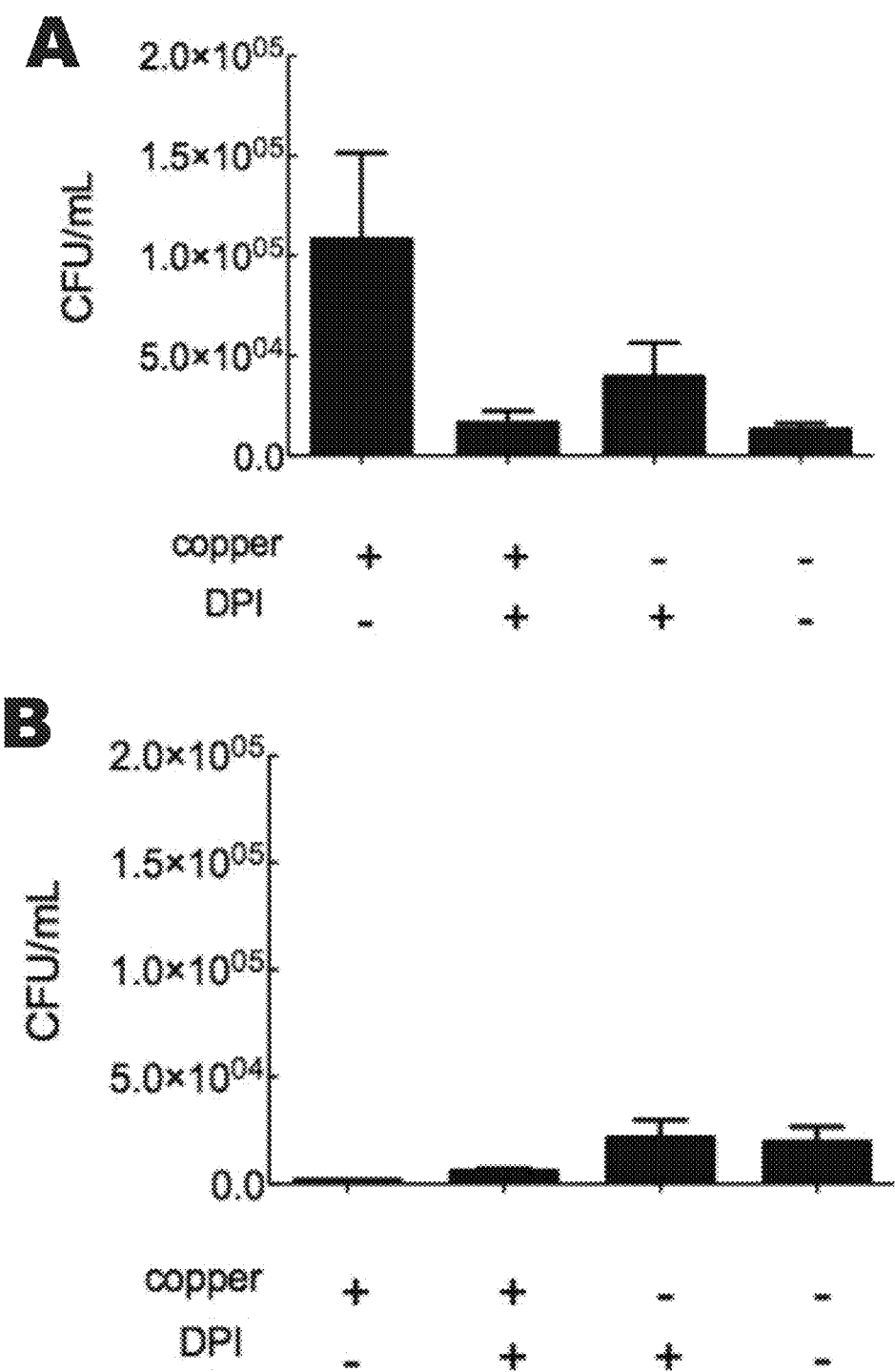

FIG. 16 Cupric yersiniabactin is a superoxide dismutase mimic that protects bacteria during the macrophage respiratory burst. RAW264.7 macrophages were treated with 25 ng/ml diphenyleneiodonium chloride in the presence or absence of 20 μm copper prior to exposure to E. coli. (A) Survival of UTI89 one hour post incubation in RAW264.7 cells is indicated. Note that UTI89 survival was significantly increased in DPI untreated, superoxide-replete RAW 264.7 cells compared with untreated controls. Copper pretreatment of these cells was additionally necessary to observe preferential survival of wild type UTI89. (B) The survival phenotype is not observed for the ybtS deficient mutant, suggesting that yersiniabactin expression predominantly contributes to the survival phenotype observed in UTI89. (C) MG1655, an E. coli commensal strain that does not express yersiniabactin, similarly does not respond to copper challenge and is susceptible to the bactericidal activity of RAW264.7 cells under all conditions tested. These results were confirmed in four independent experiments.

Figure 17:
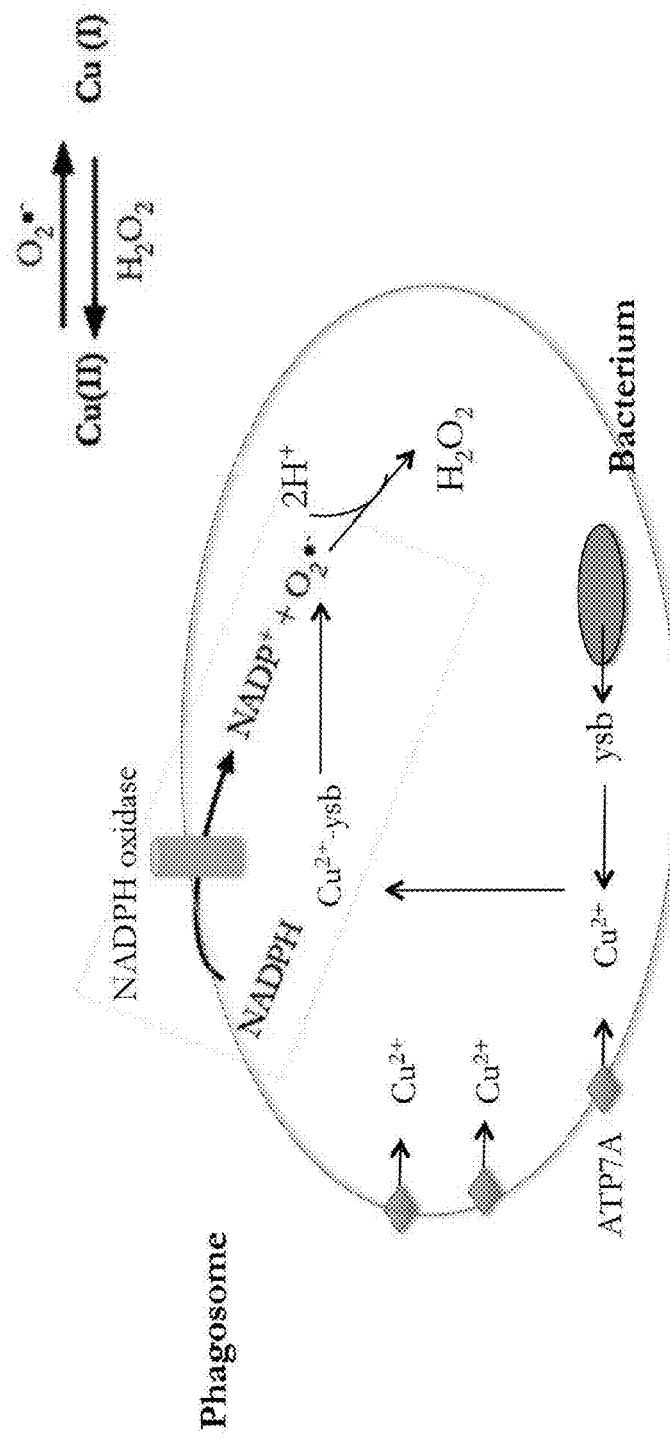

FIG. 17 Model for the interaction of copper (II) with yersiniabactin as a determinant of bacterial persistence within the phagosome. In activated macrophages, there is an upregulation of ATP7A expression and increased intraphagosomal copper levels. Additionally, this compartment relies on the generation of superoxide anion by NADPH oxidase ($\cdot O_2^-$) as its primary bactericidal species. Bacteria secrete yersiniabactin into the macrophage phagosome, which complexes copper (II). Complexes of copper (II) and yersiniabactin demonstrate SOD activity and attenuate the formation and propagation of superoxide species. The interaction of copper (II) with yersiniabactin additionally prevents downstream microbicidal effects due to disruption of Fe≠S clusters and generation of hydroxyl radicals via Fenton chemistry.

FIG. 18 The salicylate moiety of yersiniabactin interacts with superoxide species. (A) Proposed mechanism for loss of 187 amu unit from m/z 543. As previously reported, this is consistent with the rearrangement of the C13-C14 bond and loss of the third, carboxylated thiazoline ring. (B) Yersiniabactin coordinates copper (II) in a square planar configuration, with two sets of electron pairs donated by the phenolate and secondary alcohol oxygens and two from the neutral nitrogen atoms.

Figure 19:
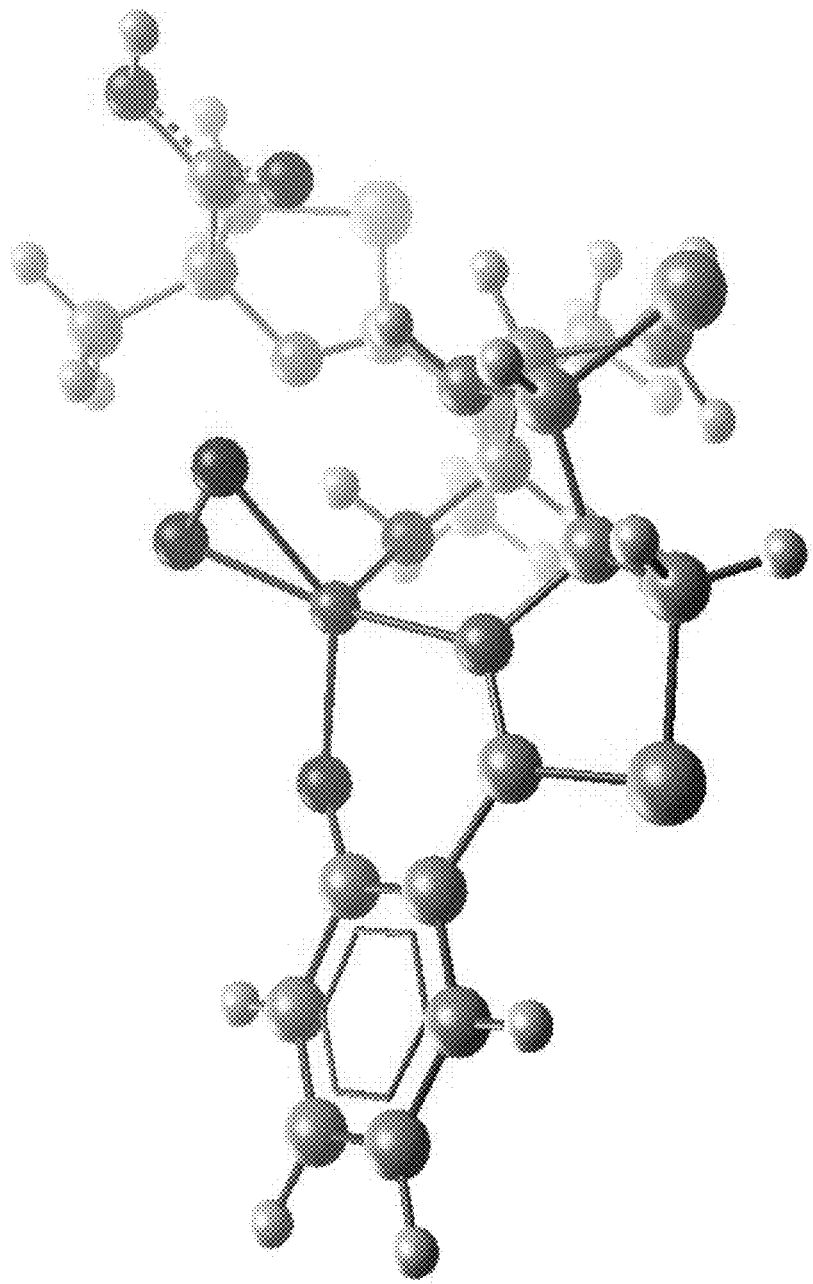

FIG. 19 Redox cycling of cupric yersiniabactin as a basis for SOD activity. DFT prediction of the superoxide adduct to the most stable form of the cupric complex, $A_0$. The cupric ion has released an OH and a NH electron pair donor in favor of maintaining a distorted square-planar geometry in which those two ligands have been replaced by the oxygens from the $O_2$ moiety. The resultant product may revert to a stable state with accompanying release of molecular oxygen.

DETAILED DESCRIPTION OF THE INVENTION

The present invention encompasses the discovery that cupric yersiniabactin is a biomarker for the presence of pathogenic bacteria in a subject. Cupric yersiniabactin is formed when pathogenic bacteria capable of producing yersiniabactin secrete yersiniabactin in a subject. The yersiniabactin subsequently interacts with copper (II) ions from the subject to form cupric yersiniabactin, a stable, detectable organometallic complex. This discovery has led to methods of detecting the present of pathogenic bacteria in a subject, and methods of determining if a subject would benefit from a yersiniabactin inhibitor.

Additionally, the invention encompasses a compound having superoxide dismutase activity. Advantageously, such a compound may be used to catalyze the dismutation of one or more superoxide radicals.

I. Methods of Detecting Pathogenic Bacteria

In one aspect, the present invention encompasses a method for detecting the presence of pathogenic bacteria in a subject. In exemplary embodiments, a method of the invention may be used to detect pathogenic bacteria in the urinary tract of a subject. Advantageously, a method of the invention avoids false negative results that occur when culture-based methods are applied during antibiotic therapy to determine the presence of pathogenic bacteria or when culture or nucleic acid-based methods are applied to subjects in which bacteria are not actively shed into sampled fluids. Generally speaking, the method comprises analyzing a sample for the presence or absence of cupric yersiniabactin, such that the presence of cupric yersiniabactin in the sample indicates the presence of pathogenic bacteria in the subject.

Furthermore, pathogenic bacteria that cause symptomatic urinary tract infection (UTI) and pathogenic bacteria that cause UT's most likely to progress to bacteremia and sepsis both secrete yersiniabactin. Thus, cupric yersiniabactin may identify not only the presence of pathogenic bacteria but may also identify patients at higher risk of progression to more severe disease.

Figure 1A:
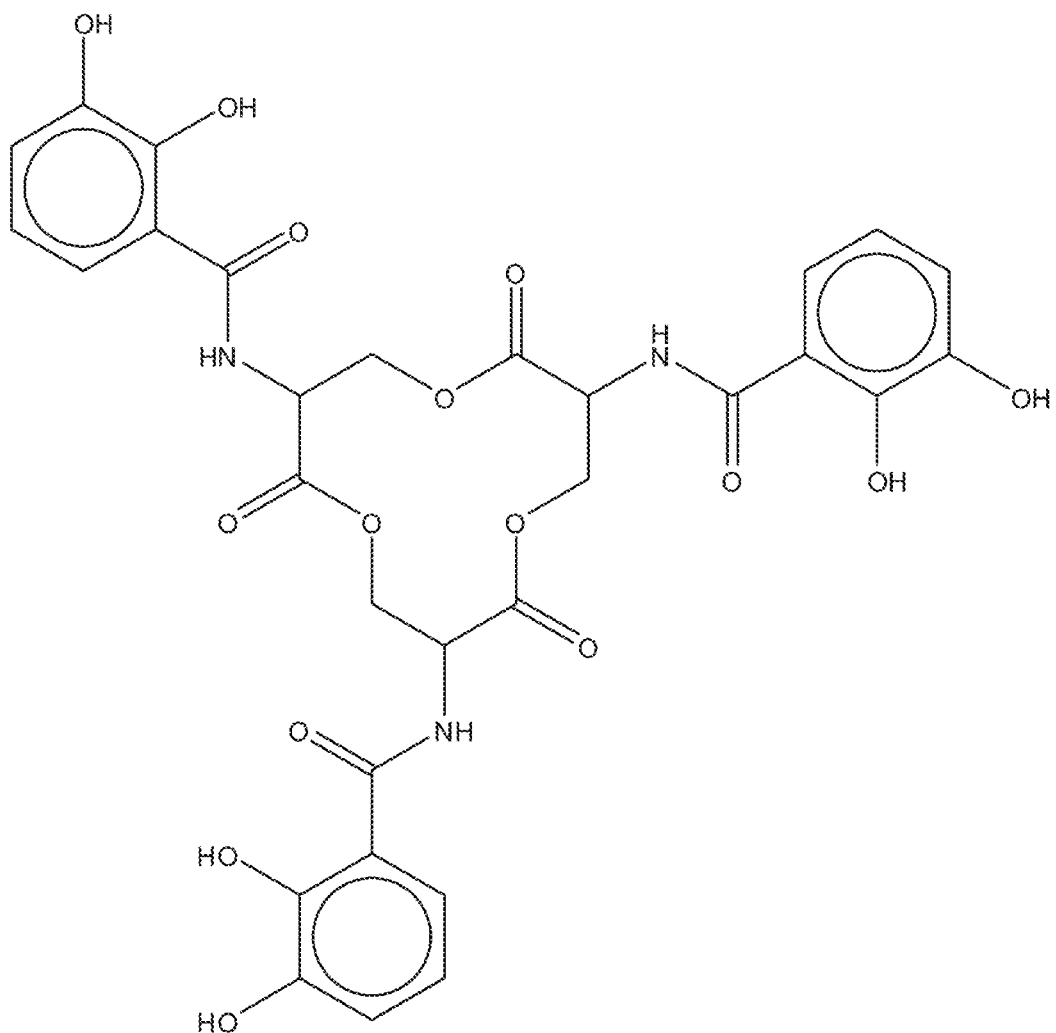
FIG. 1 *E. coli* siderophores are characterized by structural and chemical diversity. (A) the triscatecholate siderophore enterobactin and (B) the siderophore yersiniabactin, characterized by a phenolate moiety and thiazoline rings.
Figure 1B:
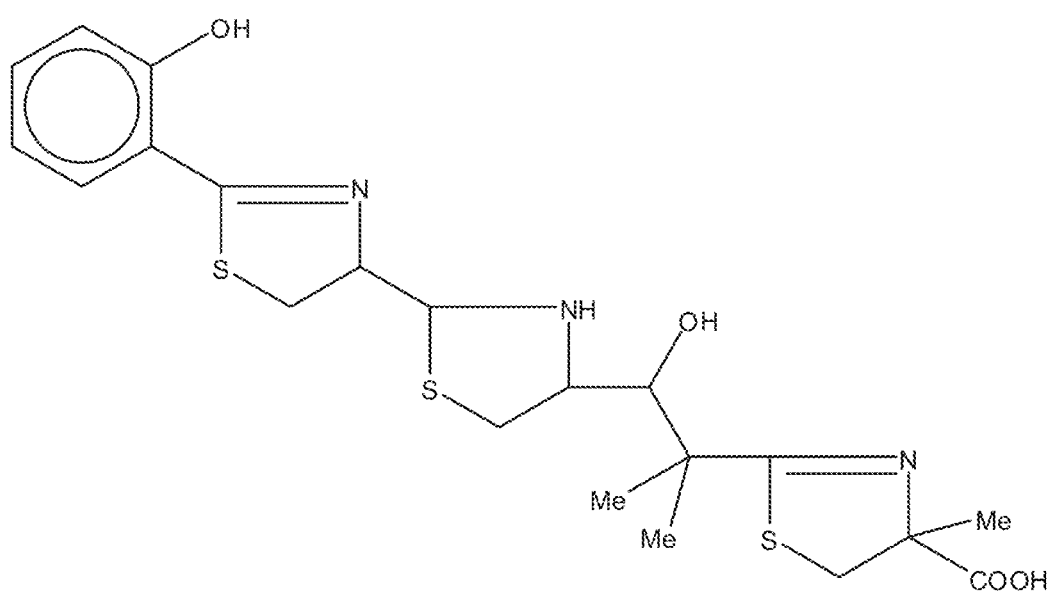

Yersiniabactin is a chemical compound comprising a four ring structure, as illustrated in FIG. 1B. Yersiniabactin, while named for being produced by pathogenic Yersinia species, is also produced by a number of other pathogenic members of the family Enterobacteriaceae. For instance, yersiniabactin may also be produced by uropathogenic bacteria capable of causing urinary tract infections or Klebsiella strains capable of causing pneumonia. In some embodiments, the invention provides a method for detecting the presence of Klebsiella strains capable of causing pneumonia in a subject. In other embodiments, the invention provides a method for detecting the presence of Yersinia species capable of causing plague in a subject.

In still other embodiments, the invention provides a method for detecting the presence of uropathogenic bacteria capable of causing urinary tract infections in a subject. Non limiting examples of uropathogenic bacteria capable of causing urinary tract infections may include uropathogenic *Escherichia coli* (UPEC) and uropathogenic *Klebsiella* species. In some embodiments, the invention provides a method for detecting the presence of uropathogenic *Klebsiella* species. In exemplary embodiments, the invention provides a method for detecting the presence of uropathogenic *Escherichia coli*.

(a) Subject

Suitable subjects for a method of the invention may include any subject capable of being infected by a yersiniabactin producing pathogen. In some embodiments, the subject may be a rodent, a human, a livestock animal, a companion animal, or a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In still another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In an exemplary embodiment, the subject is a human.

In certain embodiments, the subject may be infected by a pathogenic bacteria that produces yersiniabactin. For instance, in certain exemplary embodiments, the subject may be suffering from an acute urinary tract infection, or the subject may have a quiescent intracellular reservoir (QIR) after an acute urinary tract infection that persists even after antibiotic therapy and urine cultures become sterile. Alternatively, in some embodiments, the subject may be undergoing antibiotic therapy in which case, bacteria are not shed into sampled fluids for testing and therefore may not detected. In still further embodiments, a subject may suffer from recurrent urinary tract infections.

(b) Sample

A method of the invention comprises obtaining a sample from a subject. Generally speaking, the type of sample obtained is dependent on the type of pathogenic bacteria that is suspected. For instance, if a urinary tract infection is suspected, a urine sample may be collected. Alternatively, if a *Yersinia* infection is suspected, a lymph sample may be collected. A sample may be taken from a subject using any known device or method providing the cupric yersiniabactin is not rendered undetectable. Non-limiting examples of devices or methods suitable for taking a sample from a subject include urine sample cups, urethral catheters, swabs, hypodermic needles, thin needle biopsies, hollow needle biopsies, punch biopsies, metabolic cages, and aspiration. A suitable sample may include, but is not limited to, cerebral spinal fluid (CSF), blood plasma, blood serum, urine, saliva, perspiration, lymph, lung lavage fluid, and tears.

In a preferred embodiment, the sample is urine. Methods of collecting a urine sample are known in the art. In essence, urine may be collected mid-stream into a sterile urine sample cup. The urine sample may be treated for further analysis by adding protease inhibitors and centrifugation to remove cellular material. In addition, the urine sample may be frozen for later analysis.

(c) Analyzing a Sample

A method of the invention comprises analyzing a sample for the presence or absence of cupric yersiniabactin. Suitable methods for the detection of an organometallic compound such as cupric yersiniabactin are known in the art, and can and will vary depending upon the nature of the sample.

Methods of detecting cupric yersiniabactin may be indirect or direct. Indirect detection may comprise separating yersiniabactin from other components in the sample, or concentrating yersiniabactin in the sample, followed by detection of cupric ions in the purified or concentrated yersiniabactin sample. The presence of cupric ions in the purified yersiniabactin sample may signify the presence of cupric yersiniabactin.

In preferred embodiments, cupric yersiniabactin is detected directly by detecting the presence of the organometallic compound. For instance an epitope binding agent such as an antibody, aptamer, or other molecular beacon that recognizes cupric yersiniabactin may be used to detect yersiniabactin in the sample. In an exemplary embodiment, an antibody is used to detect the presence of cupric yersiniabactin. Other non-limiting examples of methods that may be used to detect cupric yersiniabactin in a sample may include enzyme-coupled spectrophotometric assays, HPLC, electrophoresis, and mass spectrometry.

In one embodiment, cupric yersiniabactin is detected using mass spectrometry. In particular, techniques linking a chromatographic step with a mass spectrometry step may be used. Generally speaking, the presence of cupric yersiniabactin may be determined utilizing liquid chromatography followed by mass spectrometry.

In some embodiments, the liquid chromatography is high performance liquid chromatography (HPLC). Non-limiting examples of HPLC may include partition chromatography, normal phase chromatography, displacement chromatography, reverse phase chromatography, size exclusion chromatography, ion exchange chromatography, bioaffinity chromatography, aqueous normal phase chromatography or ultrafast liquid chromatography. In one embodiment, the liquid chromatography may be ultrafast liquid chromatography.

In some embodiments, the mass spectrometry may be constant neutral loss mass spectrometry. In other embodiments, the mass spectrometry may be tandem mass spectrometery (MS/MS).

In an exemplary embodiment, the method comprises liquid chromatography followed by tandem mass spectrometry. In a particularly exemplary embodiment, the method comprises liquid chromatography followed by tandem mass spectrometry as described in the examples. In another exemplary embodiment, the method comprises liquid chromatography followed by constant neutral loss mass spectrometry. In a particularly exemplary embodiment, the method comprises liquid chromatography followed by constant neutral loss mass spectrometry as described in the examples.

In each of the above embodiments, the liquid chromatography followed by mass spectrometry may be used to determine the presence of cupric yersiniabactin in a sample, or the liquid chromatography followed by mass spectrometry may be used to determine the presence and quantity of cupric yersiniabactin in a sample. In preferred embodiments, the liquid chromatography followed by mass spectrometry may be used to determine the presence of cupric yersiniabactin in a sample.

II. Antibacterial Therapeutic

In one aspect, the present invention provides a method of treating or preventing infection by pathogenic bacteria capable of producing yersiniabactin. It was discovered that cupric yersiniabactin is associated with virulence in pathogenic bacteria that produce yersiniabactin. For instance, bacterial strains that produce yersiniabactin cause recurring or persistent urinary infections and are most likely to progress to bacteremia and sepsis. As described in the examples, cupric yersiniabactin allows the bacteria to evade the host immune responses by sequestering copper (II) originating from the host, which would otherwise be toxic to the bacteria.

Additionally, it was discovered that para-aminosalicylic acid (PAS) selectively inhibits yersiniabactin biosynthesis without inhibiting growth of the bacterium. Therefore, PAS may be used as a therapeutic or preventive treatment for diseases caused by infections with bacteria that produce yersiniabactin. In preferred embodiments, the method of treating or preventing infection by pathogenic bacteria capable of producing yersiniabactin comprises inhibiting the production of yersiniabactin by administering PAS to the subject.

In certain embodiments, PAS may be administered orally, by inhalation spray, pulmonary, intranasally, rectally, buccally, subcutaneously, intramuscularly, intrasternally intravenously, intravaginally, intrauterinely, intradermally, transdermally, or topically in dosage unit formulations containing conventional nontoxic pharmaceutically acceptable carriers, adjuvants, and vehicles as desired. Topical administration may also involve the use of transdermal administration such as transdermal patches or iontophoresis devices.

Solid dosage forms for oral administration may include capsules, tablets, pills, powders, and granules. In such solid dosage forms, PAS may be combined with one or more adjuvants appropriate to the indicated route of administration. If administered per oral solid, the compound may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. In the case of capsules, tablets, and pills, the dosage forms may also comprise buffering agents such as sodium citrate, or magnesium or calcium carbonate or bicarbonate. Tablets and pills may additionally be prepared with enteric coatings. Tablets or capsules may be coated or otherwise compounded to provide a dosage form affording the advantage of prolonged action. For example, the tablet or capsule may comprise an inner dosage and an outer dosage component, the latter being in the form of an envelope over the former. The two components may be separated by an enteric layer which serves to resist disintegration in the stomach and permit the inner component to pass intact into the duodenum or to be delayed in release. A variety of materials may be used for such enteric layers or coatings, such materials including a number of polymeric acids and mixtures of polymeric acids with such materials as shellac, cetyl alcohol, and cellulose acetate as are known in the art.

Liquid dosage forms for oral administration may include aqueous solutions, suitably flavored syrups, oil suspensions and flavored emulsions with edible oils such as cottonseed oil, sesame oil, coconut oil, or peanut oil as well as elixirs and similar pharmaceutical vehicles. Liquid dosage forms for oral administration may also include pharmaceutically acceptable emulsions, solutions, suspensions, and elixirs containing inert diluents commonly used in the art, such as water. Such compositions may also comprise adjuvants, such as wetting agents, emulsifying and suspending agents, and sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally or intrathecally acceptable diluent or solvent. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid are useful in the preparation of injectables. Dimethyl acetamide, surfactants including ionic and non-ionic detergents, and polyethylene glycols can be used. Mixtures of solvents and wetting agents such as those discussed above may also useful.

Other methods of formulating a pharmaceutical composition comprise PAS may be discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980).

Pharmaceutical compositions of the invention comprising PAS may also include pharmaceutically acceptable salts, multimeric forms, prodrugs, active metabolites, precursors and salts of such metabolites.

The term "pharmaceutically acceptable salts" refers to salt forms that are pharmacologically acceptable and substantially non-toxic to the subject being treated with PAS. Pharmaceutically acceptable salts include conventional acid-addition salts or base-addition salts formed from suitable non-toxic organic or inorganic acids or inorganic bases. Exemplary acid-addition salts include those derived from inorganic acids such as hydrochloric acid, hydrobromic acid, hydroiodic acid, sulfuric acid, sulfamic acid, phosphoric acid, and nitric acid, and those derived from organic acids such as p-toluenesulfonic acid, methanesulfonic acid, ethane-disulfonic acid, isethionic acid, oxalic acid, p-bromophenylsulfonic acid, carbonic acid, succinic acid, citric acid, benzoic acid, 2-acetoxybenzoic acid, acetic acid, phenylacetic acid, propionic acid, glycolic acid, stearic acid, lactic acid, malic acid, tartaric acid, ascorbic acid, maleic acid, hydroxymaleic acid, glutamic acid, salicylic acid, sulfanilic acid, and fumaric acid. Exemplary base-addition salts include those derived from ammonium hydroxides (e.g., a quaternary ammonium hydroxide such as tetramethylammonium hydroxide), those derived from inorganic bases such as alkali or alkaline earth-metal (e.g., sodium, potassium, lithium, calcium, or magnesium) hydroxides, and those derived from non-toxic organic bases such as basic amino acids.

The term "multimer" refers to multivalent or multimeric forms of active forms of PAS. Such "multimers" may be made by linking or placing multiple copies of an active compound in close proximity to each other, e.g., using a scaffolding provided by a carrier moiety. Multimers of various dimensions (i.e., bearing varying numbers of copies of an active compound) may be tested to arrive at a multimer of optimum size with respect to receptor binding. Provision of such multivalent forms of active receptor-binding compounds with optimal spacing between the receptor-binding moieties may enhance receptor binding. See, for example, Lee et al., (1984) Biochem. 23:4255. The artisan may control the multivalency and spacing by selection of a suitable carrier moiety or linker units. Useful moieties may include molecular supports comprising a multiplicity of functional groups that can be reacted with functional groups associated with the active compounds of the invention. A variety of carrier moieties may be used to build highly active multimers, including proteins such as BSA (bovine serum albumin) or peptides such as pentapeptides, decapeptides, pentadecapeptides, and the like, as well as non-biological compounds selected for their beneficial effects on absorbability, transport, and persistence within the target organism. Functional groups on the carrier moiety, such as amino, sulfhydryl, hydroxyl, and alkylamino groups, may be selected to obtain stable linkages to the compounds of the invention, optimal spacing between the immobilized compounds, and optimal biological properties.

"A pharmaceutically acceptable prodrug" is a compound that may be converted under physiological conditions or by solvolysis to the specified compound or to a pharmaceutically acceptable salt of such compound. "A pharmaceutically active metabolite" is intended to mean a pharmacologically active product produced through metabolism in the body of a specified compound or salt thereof. Prodrugs and active metabolites of a compound may be identified using routine techniques known in the art See, e.g., Bertolini, G. et al., (1997) J. Med. Chem. 40:2011 2016; Shan, D. et al., J. Pharm. Sci., 86(7):765 767; Bagshawe K., (1995) Drug Dev. Res. 34:220 230; Bodor, N., (1984) Advances in Drug Res. 13:224 331; Bundgaard, H., Design of Prodrugs (Elsevier Press, 1985); and Larsen, I. K., Design and Application of Prodrugs, Drug Design and Development (Krogsgaard-Larsen et al., eds., Harwood Academic Publishers, 1991). For instance, the prodrug may be any of the PAS prodrug derivatives known in the art. See, e.g., Bautzova et al., (2011) Drug Dev Ind Pharm. 37:1100-9; Lichtenstein et al., (2008) Aliment Pharmacol Ther. 28:663-73; and Simplicio et al., (2008) Molecules, 13:519-547.

The amount of PAS administered will vary depending upon the subject, the suspected pathogenic bacteria, and the particular mode of administration, and may be determined experimentally. For instance, the amount may be about 100 to 200 mg/kg/day. In some embodiments, the amount of PAS may be about 100, 110, 120, 130, 140, 150, 160, 170, 180, 190, or about 200 mg/kg/day. In other embodiments, the amount of PAS may be about 100, 101, 102, 103, 104, 105, 106, 107, 108, 109, 110, 111, 112, 113, 114, or about 115 mg/kg/day. In other embodiments, the amount of PAS may be about 110, 111, 112, 113, 14, 115, 116, 117, 118, 119, 120, 121, 122, 123, 124, or about 125 mg/kg/day. In yet other embodiments, the amount of PAS may be about 120, 121, 122, 123, 124, 125, 126, 127, 128, 129, 130, 131, 132, 133, 134, or about 135 mg/kg/day. In other embodiments, the amount of PAS may be about 130, 131, 132, 133, 134, 135, 136, 137, 138, 139, 140, 141, 142, 143, 144, or about 145 mg/kg/day. In still other embodiments, the amount of PAS may be about 140, 141, 142, 143, 144, 145, 146, 147, 148, 149, 150, 151, 152, 153, 154, or about 155 mg/kg/day. In additional embodiments, the amount of PAS may be about 150, 151, 152, 153, 154, 155, 156, 157, 158, 159, 160, 161, 162, 163, 164, or about 165 mg/kg/day. In other embodiments, the amount of PAS may be about 160, 161, 162, 163, 164, 165, 166, 167, 168, 169, 170, 171, 172, 173, 174, or about 175 mg/kg/day. In still other embodiments, the amount of PAS may be about 170, 171, 172, 173, 174, 175, 176, 177, 178, 179, 180, 181, 182, 183, 184, or about 185 mg/kg/day. In yet other embodiments, the amount of PAS may be about 180, 181, 182, 183, 184, 185, 186, 187, 188, 189, 190, 191, 192, 193, 194, or about 195 mg/kg/day. In other embodiments, the amount of PAS may be about 190, 191, 192, 193, 194, 195, 196, 197, 198, 199, or about 200 mg/kg/day. In preferred embodiments, the amount of PAS may be about 150 mg/kg/day. PAS may be administered in a single daily dose or divided into multiple daily doses. In exemplary embodiments, the amount of PAS may be about 150 mg/kg/day administered in two or three equally divided doses.

Those skilled in the art will appreciate that dosages may also be determined with guidance from Goodman & Goldman's The Pharmacological Basis of Therapeutics, Ninth Edition (1996), Appendix II, pp. 1707-1711 and from Goodman & Goldman's The Pharmacological Basis of Therapeutics, Tenth Edition (2001), Appendix II, pp. 475-493.

As used in a method herein, PAS may be administered in combination with other methods normally used to treat pathogenic bacterial infections. For instance, in some embodiments, PAS may be administered in combination with other methods normally used to treat urinary tract infections. Non-limiting examples of methods normally used to treat urinary tract infections may include the administration of antibiotics.

III. Yersiniabactin Therapeutic

Superoxide radicals ($O_2^-$) may be generated within living cells during both enzymatic and non-enzymatic oxidations. Superoxide radicals present a threat to cellular integrity; they are directly reactive, and may generate secondary free radicals that may also be reactive. Cells counter the threat of superoxide radicals by a family of defensive enzymes, superoxide dismutases (SOD) that catalyze the conversion of $O_2^-$ to $H_2O_2$ and $O_2$. The $H_2O_2$ generated by SOD is disposed of either by catalytic conversion to $O_2$ and $H_2O$ by catalases or by reduction to water at the expense of thiol, amine or phenolic substrates by peroxidases.

It has been shown that yersiniabactin complexed with a redox-active metal comprises a superoxide dismutase activity that catalyzes the dismutation of superoxide anions. In one aspect, the present invention provides a compound comprising a superoxide dismutase activity, wherein the compound is yersiniabactin complexed with a redox-active metal. Non-limiting examples of a redox-active metal may include copper and iron.

In exemplary embodiments, the compound comprising a superoxide dismutase activity is yersiniabactin complexed with copper. In exemplary embodiments, the compound comprising a superoxide dismutase activity is cupric yersiniabactin.

In other embodiments, the compound comprising a superoxide dismutase activity may be yersiniabactin complexed with iron, for instance, ferric yersiniabactin.

Yersiniabactin may be purified from bacteria capable of producing yersiniabactin or from culture supernatants of such bacteria capable of producing yersiniabactin. Alternatively, yersiniabactin may be chemically synthesized. See e.g., Roberts et al., (2010) Top Curr Chem. 297:149-203. In some embodiments, yersiniabactin is chemically synthesized. In other embodiments, yersiniabactin is purified from bacteria capable of producing yersiniabactin or from culture supernatants of such bacteria capable of producing yersiniabactin. In preferred embodiments, yersiniabactin is purified from bacteria capable of producing yersiniabactin or from culture supernatants of such bacteria as described in the Examples.

In another aspect, the invention provides a method of catalyzing the dismutation of a superoxide radical. The method comprises contacting the superoxide radical with yersiniabactin complexed with a redox-active metal. Such a method may be useful to treat, prevent, or reduce the symptoms of a condition caused by superoxide radicals. Superoxide radicals have been shown to be an important causative factor in cellular damage resulting from autoxidation, oxygen toxicity, the oxygen-dependent toxicity of numerous compounds, reperfusion injury, frostbite, an autoimmune condition, a cardiovascular condition, and inflammatory conditions. Each of which is described in more detail below. In an exemplary embodiment, the superoxide radical is produced by a macrophage or other immune system related cell.

Non limiting examples of inflammatory conditions may include allergic rhinitis, ankylosing spondylitis, arthritis, asthma, Behcet syndrome, bursitis, chronic obstructive pulmonary disease (COPD), Churg-Strauss syndrome, dermatitis, gout, Henoch-Schonlein purpura, inflammatory bowel disease (Crohn's disease or ulcerative colitis), inflammatory neuropathy, Kawasaki disease, myositis, neuritis, pericarditis, polyarteritis nodosa, polymyalgia rheumatica, prostatitis, psoriasis, radiation injury, sarcoidosis, shock, systemic inflammatory response syndrome (SIRS), Takayasu's arteritis, temporal arteritis, thromboangiitis obliterans (Buerger's disease), vasculitis, and Wegener's granulomatosis.

Autoimmune conditions are conditions caused by an immune response against the body's own tissues. Autoimmune conditions may result in destruction of one or more types of body tissues, abnormal growth of an organ, or changes in organ function. The autoimmune condition may affect only one organ or tissue type or may affect multiple organs and tissues. Non limiting examples of organs and tissues affected by autoimmune conditions may include but are not limited to blood, blood vessels, connective tissues, muscles, joints, skin, and endocrine glands. Non-limiting examples of autoimmune or autoimmune-related conditions may include Addison's disease, chronic thyroiditis, dermatomyositis, Grave's disease, Hashimoto's thyroiditis, hypersensitivity pneumonitis, insulin-dependent diabetes mellitus, insulin-independent diabetes mellitus, multiple sclerosis, myasthenia gravis, organ transplantation, pernicious anemia, Reiter's syndrome, rheumatoid arthritis, Sjogren's syndrome, systemic lupus erythematosus (SLE), thyroiditis, and urticaria.

Non limiting examples of cardiovascular conditions may include ischemia-reperfusion injury, diabetic retinopathy, diabetic nephropathy, renal fibrosis, hypertension, atherosclerosis, arteriosclerosis, atherosclerotic plaque, atherosclerotic plaque rupture, cerebrovascular accident (stroke), transient ischemic attack (TIA), peripheral artery disease, arterial occlusive disease, vascular aneurysm, ischemia, ischemic ulcer, heart valve stenosis, heart valve regurgitation, intermittent claudication, coronary artery disease, ischemic cardiomyopathy, myocardial ischemia, and ischemic or post-myocardial ischemia revascularization.

Other non limiting examples of conditions that may be caused by superoxide radicals may include cancer, sepsis, pain, cataracts, and the limited viability of transplanted organs and tissues. In some embodiments, the invention provides a method of treating sepsis. In other embodiments, the invention provides a method of treating pain. In yet other embodiments, the invention provides a method of treating cataracts. In other embodiments, the invention provides a method of treating cancer. In still other embodiments, the invention provides a method of treating stroke. In additional embodiments, the invention provides a method of treating myocardial infarction. In other embodiments, the invention provides a method of treating diabetes. In yet other embodiments, the invention provides a method of increasing the viability of transplanted organs and tissues.

As used herein, the term "treat" may be used to describe prophylaxis, amelioration, prevention or cure of a condition and/or one or more of its associated symptoms. For instance, treatment of an existing condition may reduce, ameliorate or altogether eliminate the condition, or prevent it from worsening. Prophylactic treatment may reduce the risk of developing the condition and/or lessen its severity if the condition later develops.

In yet another aspect, the invention provides a pharmaceutical composition comprising yersiniabactin complexed with a redox-active metal. Methods of administering a compound such as yersiniabactin complexed with a redox-active metal are known in the art, and are as described in Section (II).

IV. Method for Determining Whether a Subject would Benefit from a Compound that Inhibits Yersiniabactin Another aspect of the invention encompasses a method for determining whether a subject would benefit from a compound that inhibits yersiniabactin. The method comprises obtaining a sample from the subject, analyzing the sample, in vitro, for the presence or absence of cupric yersiniabactin, and identifying the subject as a subject that would benefit from a compound that inhibits yersiniabactin when cupric yersiniabactin is present in the sample.

As not all pathogenic bacteria produce yersiniabactin, it would not be beneficial to treat all suspected pathogenic bacterial infections with an inhibitor of yersiniabactin. If, however, cupric yersiniabactin were detected in a sample from the subject, then the subject is infected with a pathogenic bacteria that produces yersiniabactin, and it stands to reason that the subject would benefit from the administration of a yersiniabactin inhibitor.

Suitable samples, methods of obtaining the samples, and methods of analyzing a sample for the presence or absence of cupric yersiniabactin are as detailed above in Section I.

EXAMPLES

The following examples illustrate various iterations of the invention.

Introduction to Examples 1-10

Siderophores are a chemically diverse group of secondary metabolites used extensively by microbes—and possibly higher vertebrates—to bind and acquire ferric iron. While chemists have recognized the ability of some siderophores to bind non-ferric metal ions, investigations into pathophysiologic functions of siderophores have solely addressed their favorable interaction with ferric iron. The marked chemical diversity and differential iron binding affinities among siderophores raises the possibility that some may have evolved to bind non-ferric metal ions to fulfill additional physiologic functions. Indeed, alterations in physiologic metal composition at sites of infection may have driven bacterial pathogens to secrete siderophores with differential metal specificity to maintain fitness within the host. Understanding the functional consequences arising from this chemical coevolution between host and pathogen may provide new insights into the selective pressures driving siderophore chemistry and bacterial pathogenesis.

Genetic and metabolomic studies associate siderophore production with virulence among multiple human pathogens, particularly among *E. coli* and related Gram-negatives. Although bacterial expression of a single siderophore type is sufficient for iron acquisition in vitro, most uropathogenic *E. coli* (UPEC) express multiple siderophore types, often including the virulence-associated phenolate/thiazolidine siderophore yersiniabactin. All yersiniabactin-expressing UPEC strains described to date co-express the chemically distinct, catecholate siderophore enterobactin (FIG. 1) and occasionally the enterobactin derivative salmochelin. Epidemiologic studies suggest that *E. coli* strains that progress from bladder infection to kidney or bloodstream infection are more likely to carry the fyuA gene, a correlate of yersiniabactin producing strains. Exactly how yersiniabactin expression facilitates invasive infections has been unclear.

The examples below describe a mass spectrometry-based screen devised to determine whether non-ferric metals bind yersiniabactin in physiologically relevant fluids. This approach identified prominent copper (II) binding by yersiniabactin in human urine. Direct mass spectrometric analyses of urine from humans and mice confirm the presence of copper(II)-yersiniabactin complexes during infection with yersiniabactin-expressing strains. Functional studies demonstrate that this binding interaction is competitive with iron (III) and protects uropathogens by binding copper and preventing its catecholate-mediated reduction. Together, these studies reveal a new activity for yersiniabactin as a pathogenic countermeasure to copper-based antibacterial functions in humans.

Example 1

Figure 2A:
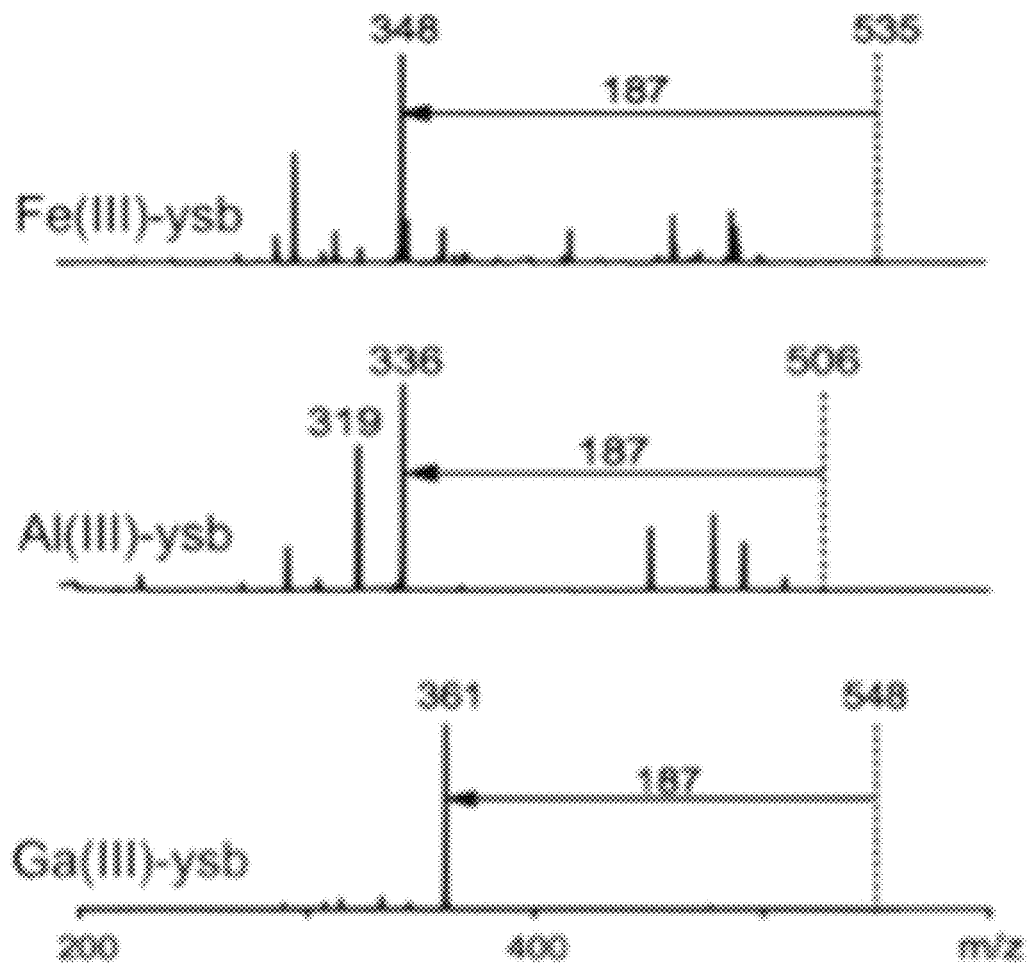
FIG. 2 A novel metal-yersiniabactin complex is revealed by a LC-constant neutral loss screen. (A) A common neutral loss of 187 amu was evident in MS/MS product ion spectra of ferric-yersiniabactin (Fe(III)-Ybt) at m/z 535, aluminum-yersiniabactin (Al(III)-Ybt) at m/z 506, and gallium-yersiniabactin (Ga(III)-Ybt) at m/z 548. (B) This 187 amu neutral loss is consistent with the proposed rearrangement and loss of the third, carboxylated thiazoline ring. A constant neutral loss (CNL) scan based on this conserved fragmentation pathway was used as a metallomic screen to identify physiologic yersiniabactin binding partners. Representative constant neutral loss chromatograms of urine samples in the presence (C) and absence (D) of purified apo-yersiniabactin are shown. The combination of apo-yersiniabactin and urine results in a prominent new peak (peak 1). Peaks corresponding to ferric-yersiniabactin (Fe—Ybt) and internal standard (int. std) are indicated. These results were confirmed in three independent experiments.
Figure 2B:
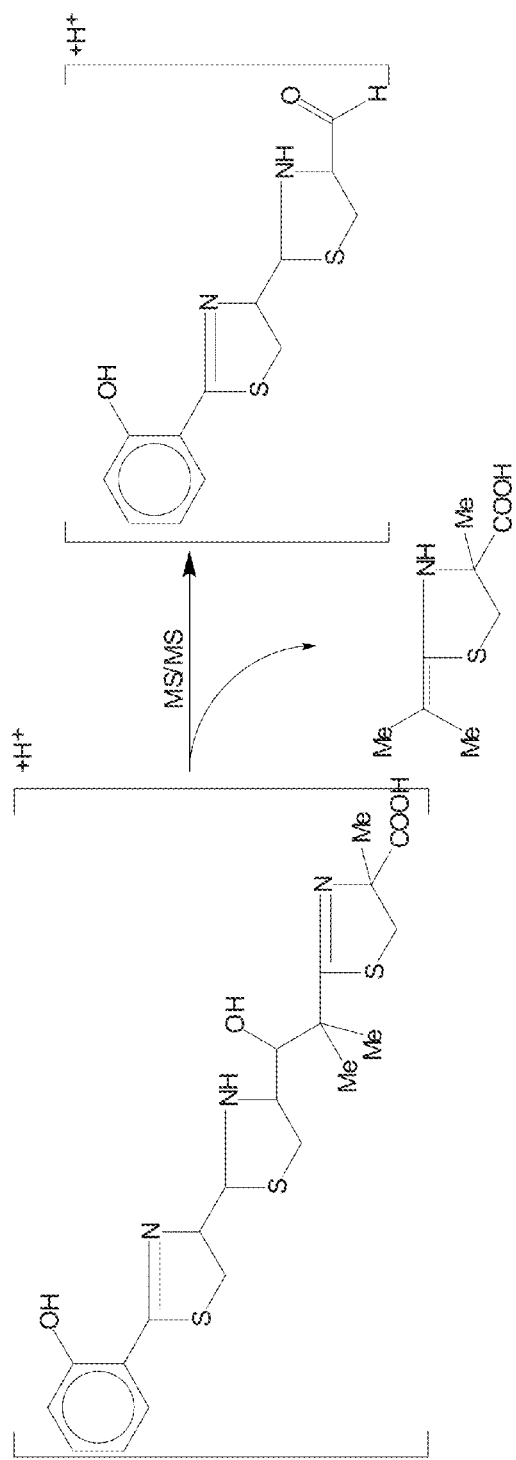
Figure 2:
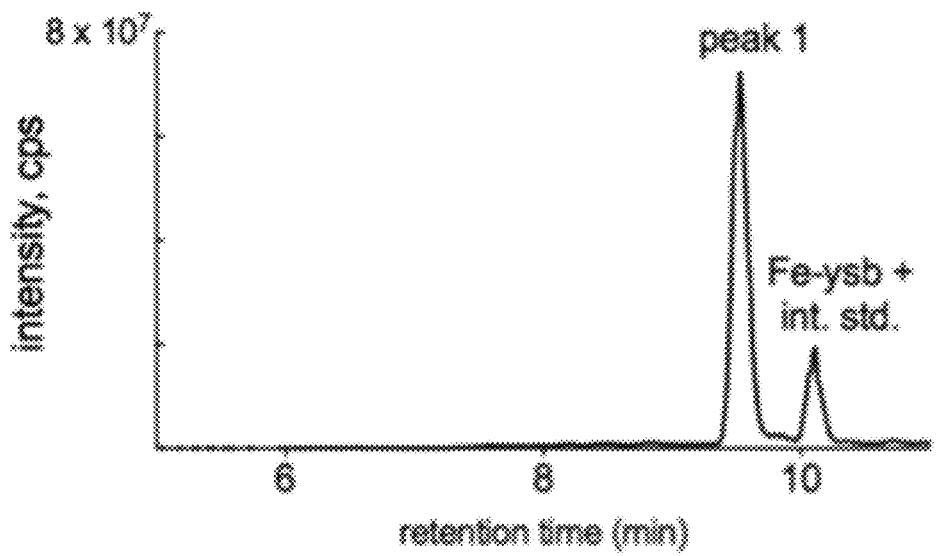
Figure 2:
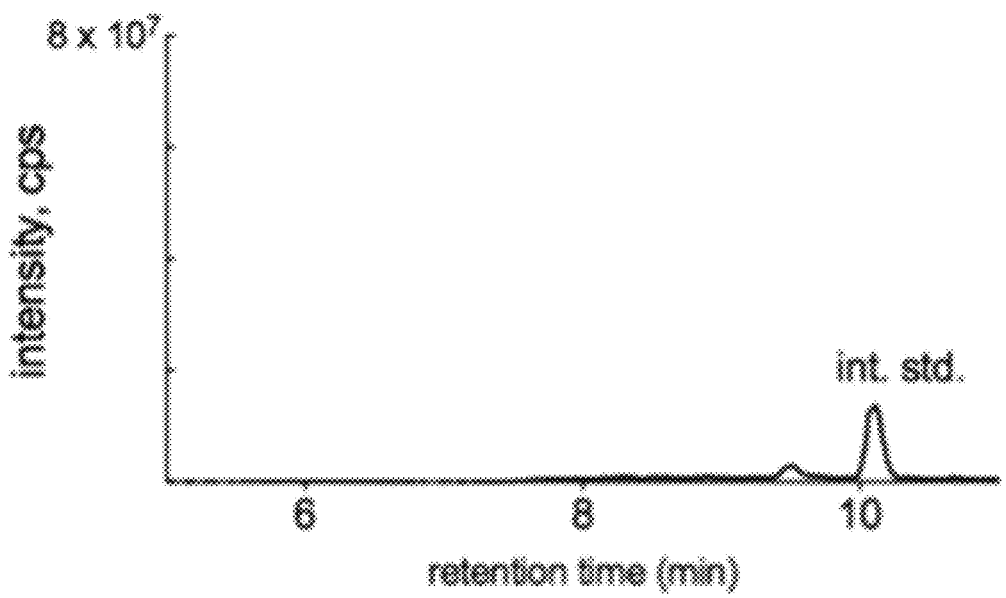

A Liquid Chromatography-Mass Spectrometry Screen Reveals a New Yersiniabactin-Metal Complex To screen for metals that bind yersiniabactin (Ybt) in a biologically relevant environment, a liquid chromatography-constant neutral loss (LC-CNL) mass spectrometric screen based on a common ion fragmentation pathway identified for model metal-yersiniabactin complexes was devised. This fragmentation pathway results in a 187 mass unit neutral loss, consistent with rearrangement of the C13-C14 bond to lose the carboxy-terminal thiazoline ($C_8H_{13}NO_2S$, FIGS. 2A and 2B). To identify biologically relevant metal-Ybt complexes, we added apo-Ybt to pooled urine samples from six healthy donors and analyzed the mixture using LC-CNL over a mass range encompassing the calculated range of naturally-occurring terrestrial metal complexes ($^6$Li to $^{239}$Pu). The LC-CNL ion chromatogram revealed formation of a dominant, novel analyte with m/z 543 (peak 1, FIG. 2C) in addition to a peak corresponding to Fe(III)-Ybt and its deuterated internal standard. The new peak 1 was absent in urine alone treated with internal standard (FIG. 2D) or when apo-Ybt was added to water (data not shown). Although urine is a highly complex mixture containing thousands of small biomolecules, the simplicity of the resulting chromatograms suggests that the 187 mass unit loss is highly specific to Ybt. Peak 1 matched no previously reported spectra, also exhibited a neutral loss of 187 mass units, and was formed by adding apo-Ybt to urine, suggesting formation of a new and biologically plausible yersiniabactin complex.

Example 2

Yersiniabactin is a Copper (II) Ligand

Figure 3:
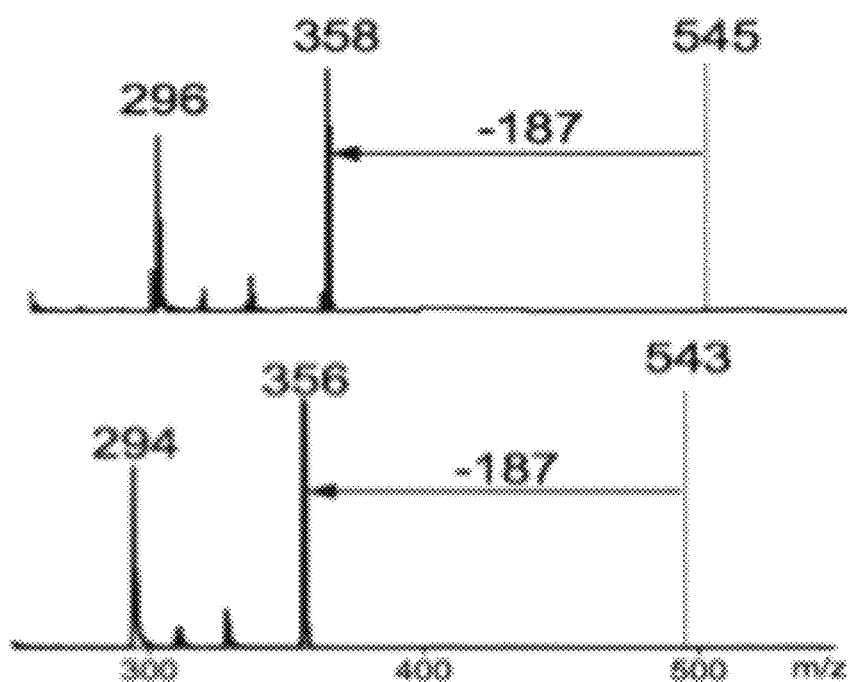
FIG. 3 Peak 1 is a stable cupric-yersiniabactin complex. (A) MS/MS analysis of the m/z 543 and 545 ions from peak 1 confirms the 187 amu neutral loss and shows comparable fragmentation patterns, consistent with natural $^{63}Cu$ and $^{65}Cu$ isotope abundances. Addition of cupric sulfate to yersiniabactin-containing culture supernatant generated a robust new peak 1 signal, which was collected for analysis. (B) High resolution positive ion ESI mass spectrum is consistent with the empiric formula for singly charged Cu(II)-Ybt and demonstrates the prominent M+2 ion expected from $^{65}Cu$. (C) Competitive binding experiments were conducted by titration of cupric sulfate into solutions containing a fixed concentration of 0.01 M ferric chloride and 0.01 M apo-yersiniabactin. Data indicate competitive binding between cupric and ferric ion for the ligand. Cu(II)-Ybt/Fe(III)-Ybt ratios were quantified by generating a calibration curve of known ratios of each metal-yersiniabactin complex, and analyzing the samples by LC-MS. (D) Cu(II)-Ybt complexes are stable and bound copper is not displaced by ferric ions over a period of 24 hours. Cu(II)-Ybt is expressed as its ratio to trace Fe(III)-Ybt impurity in apo-Ybt.
Figure 3:
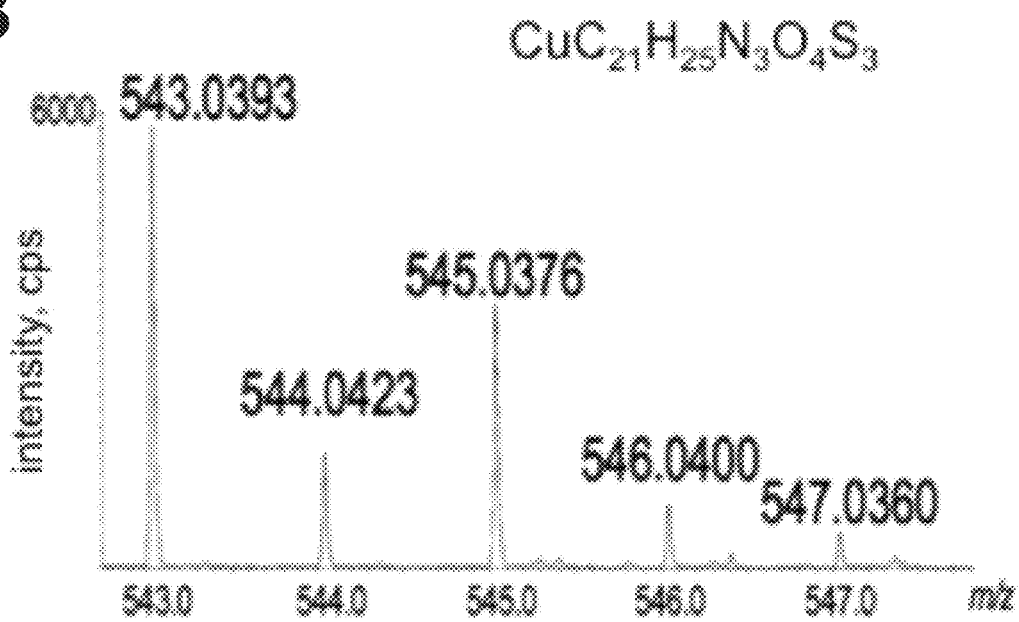
Figure 3:
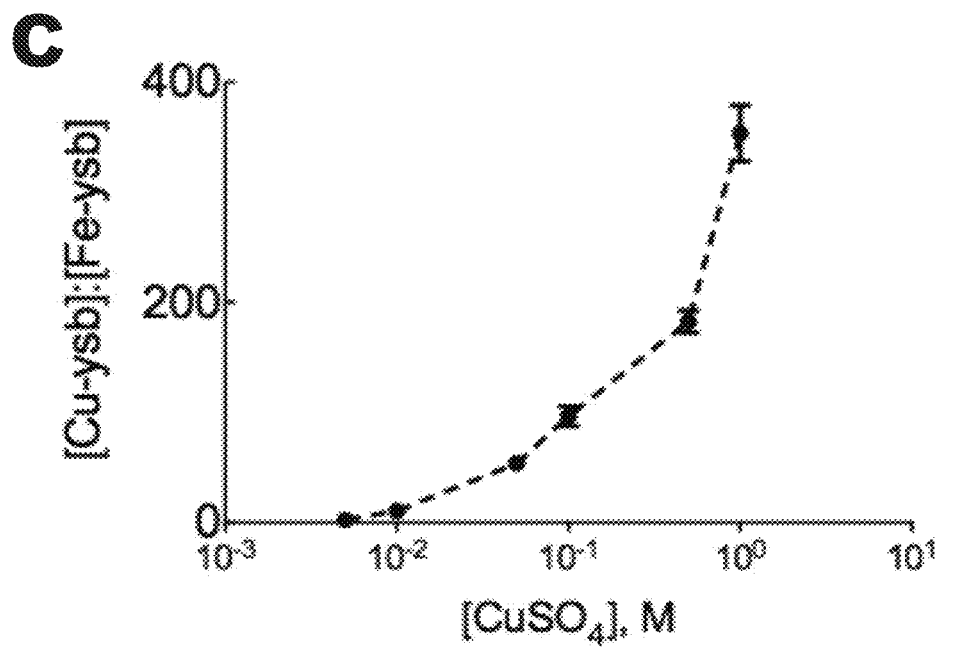
Figure 3:
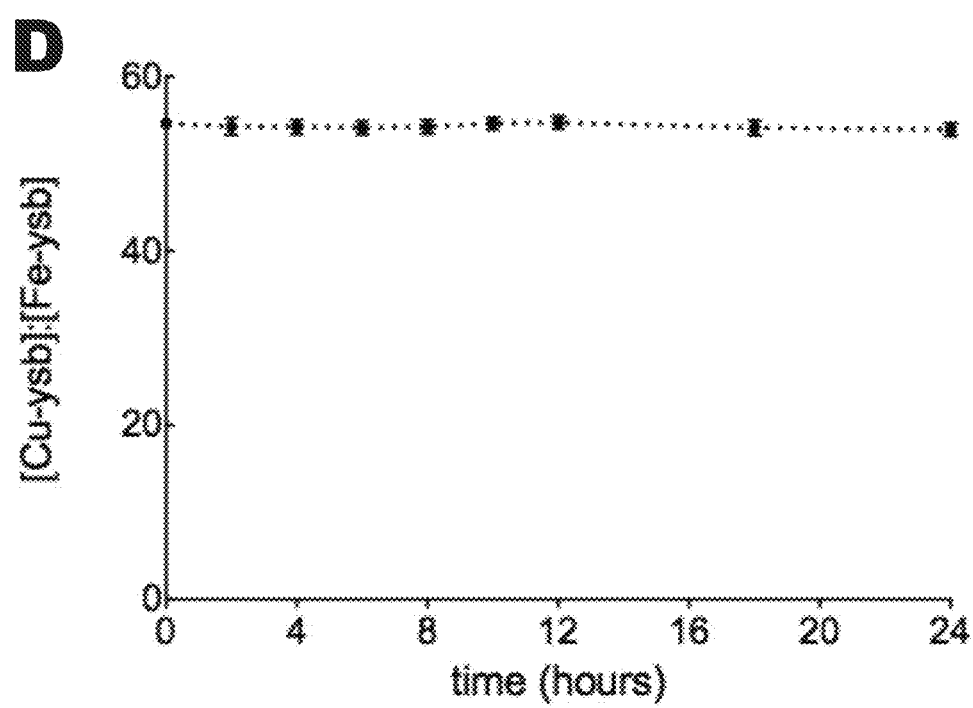

Peak 1 was first subjected to additional mass analyses. The CNL mass spectrum of this complex exhibited a prominent M+2 peak at m/z 545, approximately one third the height of the base peak. MS/MS analysis of the M and M+2 peaks at m/z 543 and 545 exhibited product ion spectra with identical fragmentation patterns differing by 2 mass units (FIG. 3A). The apo-Ybt spectrum lacks this prominent M+2 peak, suggesting a prominent isotope pattern contribution from the unknown Ybt binding partner. A Ybt-derived base peak ion 61 mass units higher than the Ybt $[M+H]^+$ ion with a prominent M+2 isotope peak was consistent with a singly charged cupric complex of the form $[Ybt+Cu(II)-H]^+$. The observed isotopic pattern is consistent with the natural $^{63}$Cu and $^{65}$Cu isotope abundances of 77% and 23%, respectively. The m/z value of this complex is consistent with the presence of copper (II), rather than copper (I), which would require an additional proton to yield a singly charged ion at m/z 544, rather than the observed 543.

Further confirmation was pursued by adding molar excess of copper (II) sulfate to UTI89 ΔentB (which produces Ybt as the only siderophore) culture supernatant, followed by preparative chromatography. Application of this copper(II)-treated supernatant to a preparative C18 column resulted in retention of a blue colored fraction on the column that was eluted with 80% methanol. The LC-MS chromatogram of this blue fraction was dominated by peak 1. This fraction was subjected to accurate mass determination on a Bruker Q-TOF Maxis using positive ion electrospray mode, which again showed the prominent M+2 ion and supported the formula $C_{21}H_{25}CuN_3O_4S_3$ for peak 1 ion at 543.0393 (FIG. 3B). The presence of 21 carbons was confirmed by detection of $^{13}$C-labeled peak 1 at m/z 564 in supernatants from bacteria grown in $[^{13}C_3]$ glycerol. MS/MS of this peak 1 isotopologue revealed a new dominant MS/MS neutral loss of 195 mass units, supporting the proposed common $C_8H_{13}NO_2S$ neutral loss. Together, these results support the identity of peak 1 as a stable copper (II) complex of Ybt that forms spontaneously when Ybt is exposed to physiologic concentrations of copper in human urine.

Example 3

Copper(II) Competes with Iron (III) in Solution to Produce a Stable Cu(II)-Ybt Complex To determine whether cupric and ferric ion species bind competitively to Ybt, relative copper(II)— and iron(III)-yersiniabactin (Cu(II)-Ybt and Fe(III)-Ybt, respectively) yields were quantified in competitive binding experiments. Increasing concentrations of cupric sulfate were added to PBS containing 0.01 M ferric chloride at pH 7.0 at 25° C. for one hour (FIG. 3C). One micromolar apo-yersiniabactin was then added to these samples and the Cu(II)-Ybt/Fe(III)-Ybt ratio was determined by LC-MS following a two-hour incubation. The Cu(II)-Ybt/Fe(III)-Ybt ratio exhibited a positive correlation with copper (II) concentration, consistent with competitive binding between aqueous cupric and ferric species.

To determine whether iron displaces copper from Cu(II)-Ybt complexes in our experimental conditions, we monitored an extended time course of Cu(II)-Ybt levels in the presence of ferric ions. Twenty five micromolar apo-Ybt was incubated with 25 μM cupric sulfate for one hour to form Cu(II)-Ybt. Next, 0.025 M competing ferric chloride was added and the resulting Cu(II)-Ybt level was followed over a 24 hour time course (FIG. 3D). The Cu(II)-Ybt level was unchanged, consistent with a low rate of ferric ion displacement in our analytical and experimental conditions.

Example 4

Figure 4:
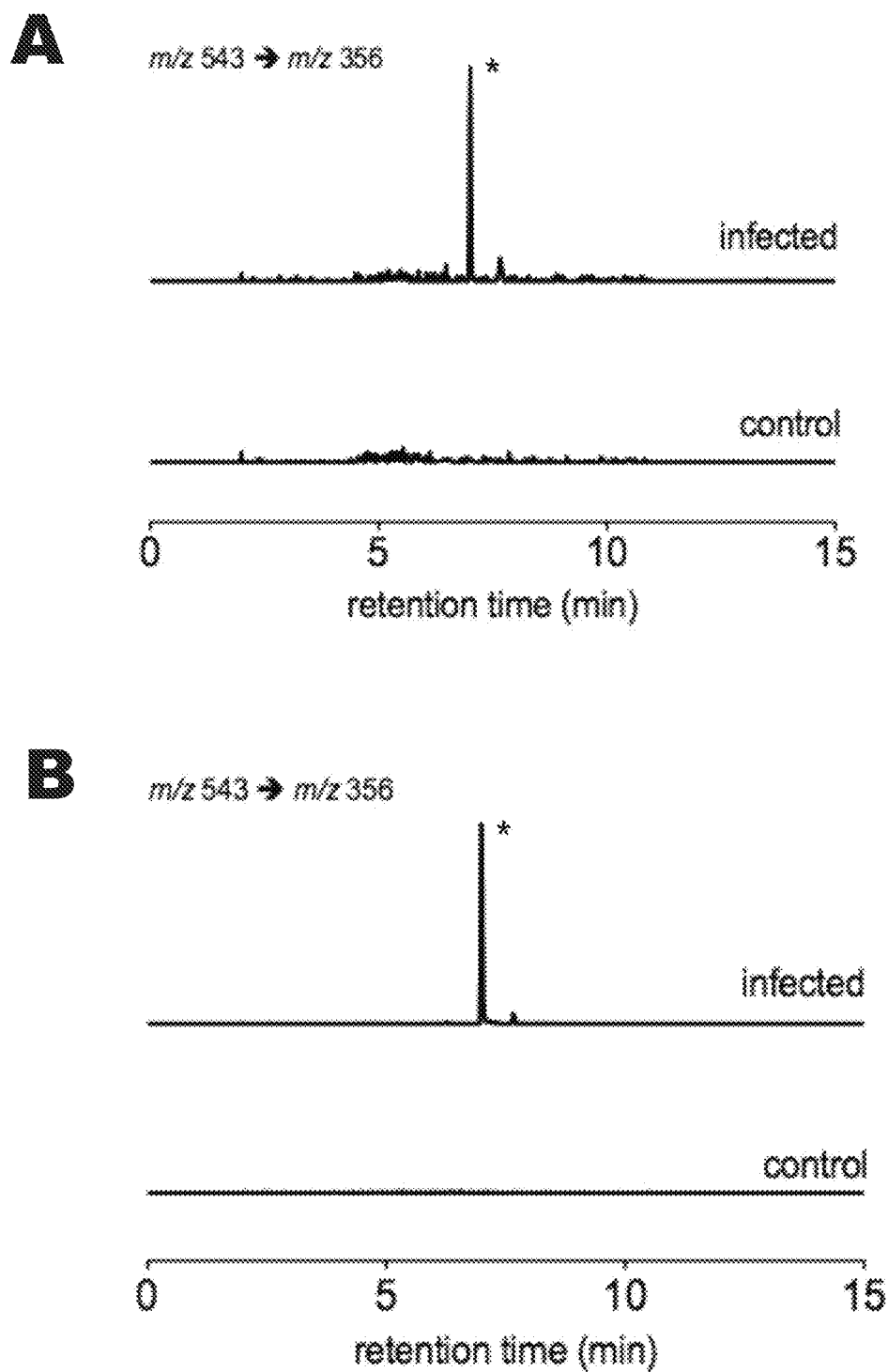
FIG. 4 Cupric-yersiniabactin forms in murine bladder tissue and urine during experimental uropathogenic *E. coli* cystitis. Bladder tissue and urine were collected from infected mice and prepared for mass spectrometric analysis. Shown are MS/MS chromatograms showing Cu(II)-Ybt peaks in (A)
Figure 4C:
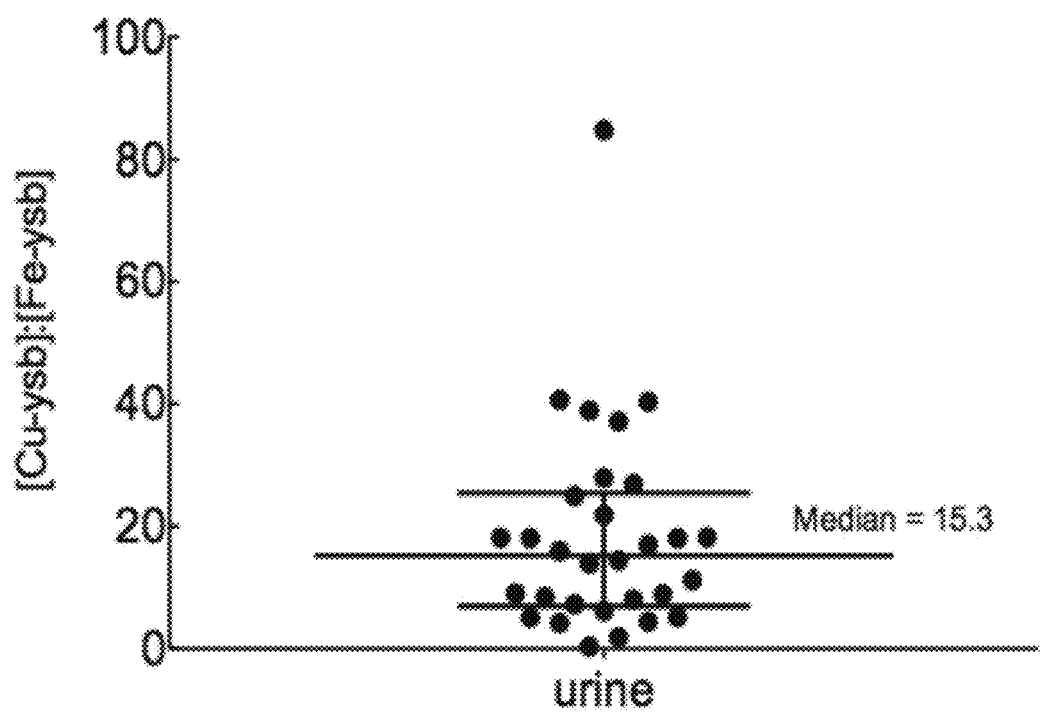

Urine and Tissue Extracts from Murine *E. Coli* UTI Demonstrate In Vivo Cupric-Yersiniabactin Formations To determine whether Ybt is expressed and binds copper during infection, LC-MS/MS was used to analyze murine urine and bladder tissue following experimental infection with the model uropathogen UTI89. A strong signal with the expected Cu(II)-Ybt MS/MS transition and retention time was observed in all 30 bladder tissue and urine sample from infected, but not mock infected, mice 24 hours after pathogen inoculation (FIGS. 4A and 4B). The median Cu(II)-Ybt/Fe (III)-Ybt molar ratio was 15.3 (range=0.38-84.8) (FIG. 4C). 29 of 30 (97%) urine samples from infected mice exhibited a Cu(II)-Ybt/Fe(III)-Ybt molar ratio >1, consistent with favorable in vivo Cu(II)-Ybt formation. These findings demonstrate that a typical urinary pathogen expresses Ybt during murine infections, and that a greater abundance of copper (II) complexed siderophore is subsequently detected in biological samples derived from infected mice.

Example 5

Cupric-Yersiniabactin Complexes Form During Human UTI

To determine whether Ybt is expressed and binds copper during human urinary tract infections, 32 midstream urine samples from a cohort of women with acute cystitis were analyzed for Cu(II)-Ybt. LC-MS/MS analysis of cultured urinary pathogen isolates from these patients confirmed infection by a Ybt-expressor in 15 out of 32 subjects. Scanning neutral loss analysis of urine from a patient infected with a Ybt-expressing strain revealed a strong Cu(II)-Ybt signal with the expected m/z 543 ion and its characteristic $^{65}$Cu isotopomer at m/z 545, confirming in vivo formation of Cu(II)-Ybt (FIG. 5A). Quantitative analysis using $^{13}$C-labeled internal standards demonstrated significantly (p<0.0001) higher urinary Cu(II)-Ybt levels in patients infected with Ybt expressors (13/15 positive) than in patients infected with non-expressors (0 of 17 positive) (FIG. 5B). Together, these data demonstrate that uropathogenic *E. coli* can express Ybt during human urinary tract infections and that this Ybt binds host-derived copper.

Figure 5C:
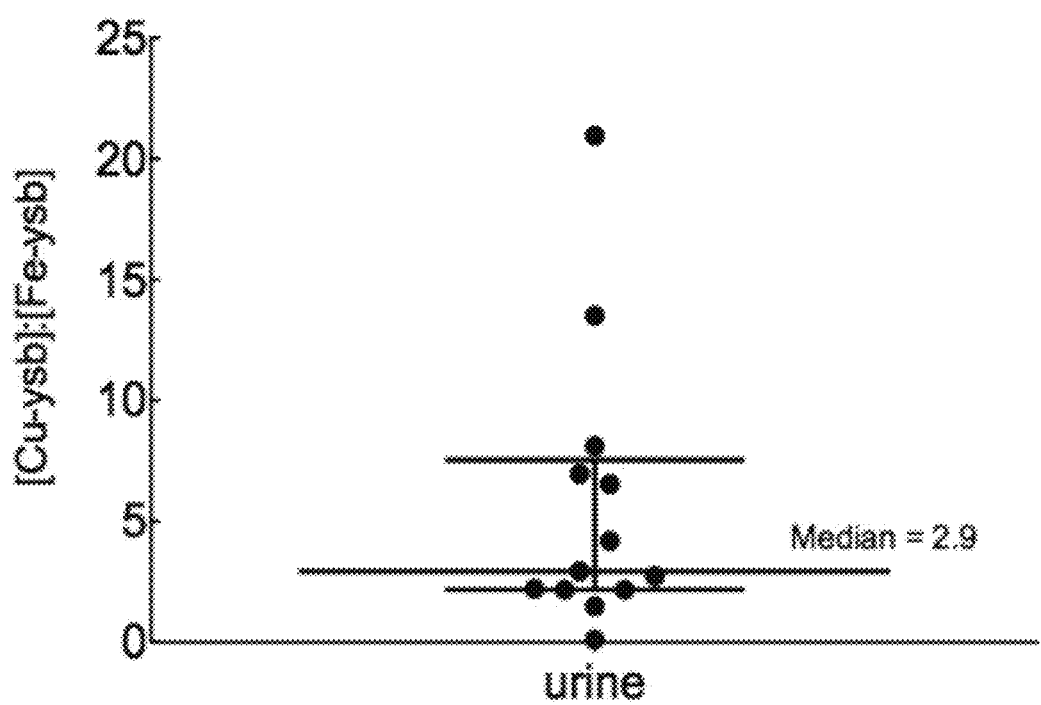

To determine whether the extent of in vivo copper and iron binding was similar, the Cu(II)-Ybt/Fe(III)-Ybt molar ratio in urine was measured. In the 13 samples with detectable Ybt complexes, the median Cu(II)-Ybt/Fe(III)-Ybt ratio was 2.9 (range=0.12-20.9) (FIG. 5C) with 92% (12/13) patients exhibiting a molar ratio >1. These data indicate that Ybt binds host-derived copper at least as extensively as ferric iron during human infections.

Example 6

Yersiniabactin Expression is Associated with Increased Copper Resistance Among Infection-Associated *E. Coli* Isolates Copper ions are toxic to *E. coli* and other bacteria at low micromolar concentrations. By binding copper ions, Ybt may act as a pathogenic countermeasure to copper toxicity. To determine whether copper resistance is a virulence correlate, the effects of copper on bacterial growth in a previously described collection of co-existing urinary and non-urinary *E. coli* isolates from 13 UTI patients was measured. These experiments were conducted within the normal serum copper concentration range of 10 μM. This analysis revealed that the *E. coli* strains infecting the urinary tract were significantly (p<0.0005) more copper resistant than coexisting non-urinary strains from the same patients with 10 out of 13 urinary isolates exhibiting >$10^7$ higher CFU/mL (FIG. 6A).

It is known from previous work that 10 of 14 urinary isolates and 6 of 18 non-urinary isolates produce Ybt. When growth in copper-supplemented media was grouped by Ybt expression, the Ybt-expressors exhibited significantly (p<0.0013) greater copper resistance (FIG. 6B). Together, these data show that urinary isolates exhibit greater copper resistance than non-urinary isolates in a UTI patient population and that enhanced copper resistance is strongly associated with Ybt production.

Example 7

Endogenous Yersiniabactin Production Protects Bacteria from Copper Toxicity

Figure 6C:
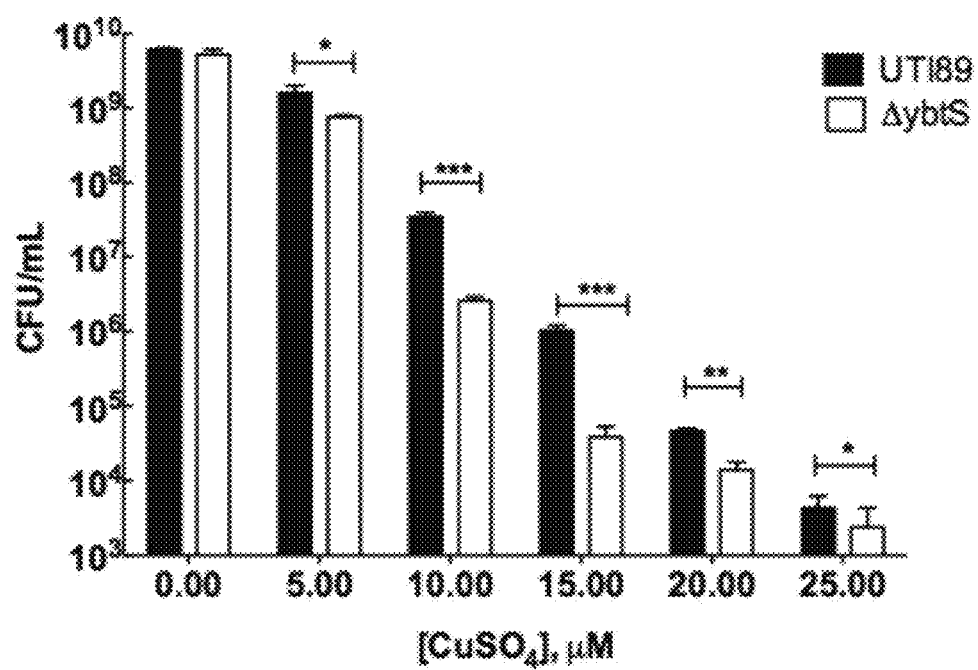

To determine whether Ybt production has a functional impact on copper resistance, the Ybt-deficient mutant UTI89ΔybtS was compared to the wild type uropathogen control UTI89. After an 18 hour incubation, copper (II) sulfate inhibited UTI89ΔybtS growth significantly more than that of wild type UTI89. Over a range of 5 to 25 μM copper (II) sulfate, wild type cultures yielded an average of 1.34 log more CFUs than UTI89ΔybtS cultures (p=0.0032, FIG. 6C). To confirm that Cu(II)-Ybt is expressed in this experimental system, LC-MS analysis of culture supernatants treated with 25 μM copper (II) sulfate was performed. Cu(II)-Ybt complexes were observed in wild type, but not UTI89ΔybtS, conditioned media (data not shown). Together, these findings show that intact Ybt gene plays a mechanistic role in copper resistance.

Example 8

Exogenous Apo-Yersiniabactin Protects Bacteria from Copper Toxicity

Figure 6D:
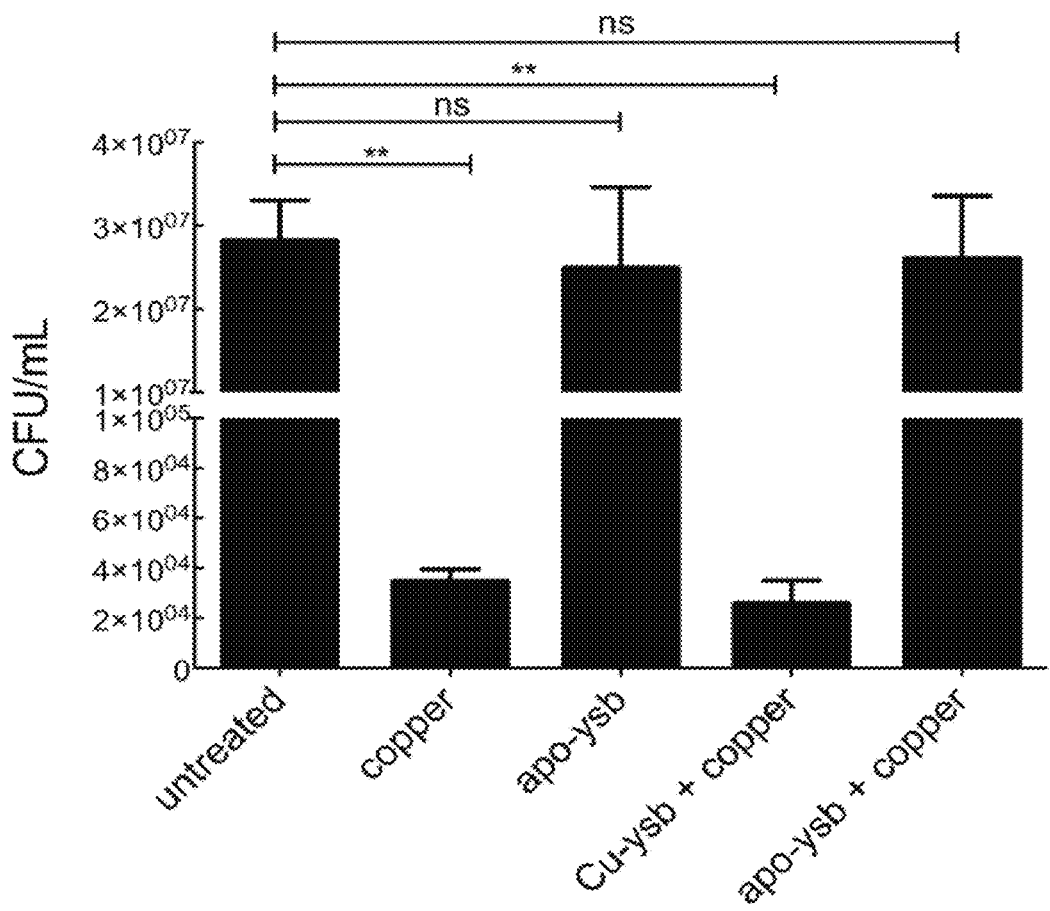

To determine whether Ybt directly protects bacteria from copper toxicity, the effect of purified apo-Ybt on viability of UTI89ΔybtS (Ybt biosynthesis mutant) cultures exposed to 10 μM copper sulfate was examined (FIG. 6D). Copper addition alone resulted in a substantial >3 log CFU/mL decrease in bacterial viability. Apo-Ybt protected copper-treated bacteria almost completely from cytotoxicity, with only a 0.024 log decrease in viable cells compared to wild type (p=NS). Addition of pre-formed Cu(II)-Ybt complexes abolished the protective effect, suggesting that an unoccupied copper-binding site on apo-Ybt is required for cytoprotection. In the absence of copper, apo-Ybt alone had a negligible effect on bacterial viability. These results show that copper-binding by exogenous Ybt directly protects bacteria from copper toxicity.

Example 9

Yersiniabactin or Enterobactin-Deficient Mutants Exhibit Opposing Alterations in Copper Sensitivity To determine whether other UPEC siderophores affect copper susceptibility, copper toxicity in an established UTI89 mutant with defined siderophore deficiencies was evaluated (FIG. 7A). As noted above, UTI89ΔybtS was more susceptible to copper than the wild type strain (p=0.0021). Conversely, additional deletion of the catecholate biosynthesis gene entB in this strain background (an ΔentBΔybtS double mutant), significantly (p=0.0032) increased survival. The single ΔentB mutant, which expresses Ybt, exhibits a supraphysiological survival benefit in the presence of copper. These results are consistent with previous work describing copper (II) reduction by catechols to more toxic copper (I) ions.

Example 10

Yersiniabactin-Complexed Copper (II) Resists Catechol-Mediated Copper (I) Formation To test whether the absence of copper reduction by catecholate siderophores explains increased copper resistance in the UTI89ΔentB mutant, we examined copper toxicity to UTI89 in the presence and absence of enterobactin or 2,3-dihydroxybenzoic acid (DHB), the catecholate moiety incorporated into enterobactin and salmochelin. Treatment with 10 µM copper (II) sulfate alone caused a 2.5 log reduction of viable colonies. While 20 µM enterobactin or DHB alone had a minimal effect, their addition to copper (II) sulfate significantly ($p<0.0072$ and $p<0.0039$, respectively) increased copper cytotoxicity, decreasing viable cells to below the level of detection (LOD=20 CFU/mL) (FIG. 7B). These data show that antibacterial synergy between enterobactin and copper (II) is attributable to enterobactin's catecholate groups.

To confirm that enterobactin reduces copper (II) and to determine whether Ybt affects this reaction, copper (I) formation was monitored by purified reagents using a bathocuproine-based spectrophotometric assay (FIG. 7C, D). Addition of either 20 µM enterobactin or DHB to samples containing 17.5 µM copper (II) sulfate resulted in a strong bathocuproine signal corresponding to 84.7% and 93.1% reduction of copper (II) to copper (I), respectively. This signal was almost completely blocked when apo-Ybt was added before enterobactin or DHB. In contrast, changing the order of addition such that enterobactin or DHB were added before apo-Ybt restored the copper (I) signal. Together, these results demonstrate that the catecholate groups of enterobactin and related siderophores reduce copper (II) to more cytotoxic copper (I) and that yersiniabactin protects bacteria not only by sequestering copper (II) but also by inhibiting its catecholate-mediated reduction.

Discussion for Examples 1-10

Results described in the Examples above demonstrate that yersiniabactin binds copper in vivo and protects uropathogenic E. coli from host-derived copper, whose toxicity is enhanced by co-expressed siderophores. Physiologic relevance of copper binding is demonstrated by direct unbiased chemical detection of Cu(II)-Ybt in tissue and urine from an experimental animal infection model and in urine derived from patients with E. coli urinary tract infection. Furthermore, although yersiniabactin and catecholate siderophores have been previously regarded as redundant iron acquisition molecules, this study shows that they can assume disparate roles in modulating copper chemistry and toxicity at the host-pathogen interface. These results suggest that the chemical biology of pathogenic siderophores extends beyond issues of iron binding and acquisition.

Precedent for microbial copper chelation is found among environmental bacteria. While not a siderophore, methanobactin serves an analogous function by binding Cu(I) to satisfy a high nutritional copper requirement driven by synthesis of particulate methane monooxygenase, which accounts for up to 20% of methanotrophic bacterial proteins. The algal hydroxamate siderophore schizokinen may weakly bind Cu(II), with differing effects on copper toxicity to environmental bacteria. Although data in these Examples are consistent with protective copper sequestration as a yersiniabactin function, yersiniabactin could benefit bacteria by obtaining copper as a nutritional source under other circumstances. Yersiniabactin's ability to bind copper during infection may thus derive from an ancestral function or reflect an example of convergent chemical evolution.

Although copper resistance proteins have been described in a wide variety of bacteria, it is unclear if copper resistance represents a virulence-associated adaptation. This question is readily addressed in E. coli, where disease-associated strains exhibit evidence of multiple virulence-associated adaptations. By demonstrating enhanced copper-resistance among disease-associated isolates, this study suggests an important role for copper ions as an antimicrobial defense in human UTI pathogenesis. A role for copper-based immune defenses is further supported by observations of infection-associated increases in copper and use of copper transporters by phagocytic cells to kill internalized bacteria. It is possible that disease-associated isolates without high level copper resistance (4/14 isolates in the present examples) are indicative of patients with subtle differences in pathophysiology or copper-based antimicrobial responses (FIG. 6A). Regardless, the sum of bacteriologic and bioanalytic findings suggests a role for host-derived copper as a virulence-associated selection factor among uropathogenic E. coli.

While catechols are excellent iron-binding functional groups, their ability to directly reduce cupric ions provides a chemical rationale for acquisition of non-catecholate siderophores by bacterial pathogens. Copper (II) is significantly more bactericidal when reduced to its copper (I) valence, which has been attributed to an improved ability of copper (I) to generate reactive oxygen species or to freely penetrate bacterial membranes and inactivate intracellular iron-sulfur clusters. Thus, yersiniabactin's ability to prevent copper (II) reduction and intracellular penetration may additionally protect pathogenic bacteria during infection. Targeting yersiniabactin biosynthesis or the strains that perform this may thus be a useful therapeutic approach. Although it is unclear which yersiniabactin coordination sites facilitate copper binding, it is notable that this molecule contains three nitrogenous heterocycles (thiazolines/thiazolidine), reminiscent of imidazole-rich copper coordination sites in ceruloplasmin and the nitrogen heterocycles in methanobactin. Similar structural features in other siderophores and microbial products may facilitate similar copper-binding functions.

Siderophore profiling by mass spectrometric methods has yielded important insights into the pathogenicity of E. coli and other important pathogens. To date, neither pathogenic siderophore secretion nor in vivo metal ion selectivity of these siderophores have been directly observed and quantified. This work shows how tandem mass spectrometry, together with an understanding of gas phase ion chemistry, can also identify metal binding interactions of these diverse molecules. Its notable sensitivity also permits use of LC-MS/MS to directly interrogate in vivo metal binding rather than relying solely upon attempts to simulate in vitro the complex metal availabilities at sites of infection.

Bacterial pathogens have adapted to a shifting array of evolutionary challenges by secreting a chemically diverse range of secondary compounds and proteins. Yersiniabactin may be one of many multifunctional, virulence-associated metal binders secreted by pathogenic bacteria. In future studies, similar binding interactions could be discovered and validated for other important biomolecules or other secondary compounds using an analogous chemical biology approach.

Materials and Methods for Examples 1-10

Bacterial Strains, Cultivation and Deletion Strain Construction

Urinary and rectal isolates are from a previously described collection. Briefly, distinct, coexisting strains were identified by pulsed-field gel electrophoresis (PFGE) from a longitudinal patient study. Strains were not considered to be "rectal" if they were isolated from a urinary source at any time during the study.

UTI89, a well characterized and fully sequenced uropathogenic *E. coli* clinical isolate, was used as the prototypic pathogen in this study. UTI89 mutant strains used in the Examples are listed in Table 1. Bacterial cultures were grown from a single colony in Difco™ Luria-Bertani broth, Miller (LB) (BD, Franklin Lakes, N.J.) for three hours and subsequently diluted 1:100 into M63 medium supplemented with 0.2% glycerol and 10 mg/mL niacin (Sigma). Bacterial cultures were incubated for 18 hours at 37° C. in a rotary shaker.

TABLE 1

UTI89 mutant strains used in this study

| Strain | Gene function | Reference |
| --- | --- | --- |
| UTI89ΔybtS | salicylate synthase, yersiniabactin biosynthesis | Henderson et al. 2009, PLoS Pathog 5, e1000305 |
| UTI89ΔentB | isochorismate lyase, catecholate siderophore (enterobactin/salmochelin) biosynthesis | Henderson et al. 2009, PLoS Pathog 5, e1000305 |
| UTI89ΔiroA | salmochelin biosynthesis, transport, catabolism | Henderson et al. 2009, PLoS Pathog 5, e1000305 |
| UTI89ΔentBΔybtS | salicylate synthase, isochorismate lyase, total mutant for yersiniabactin, enterobactin and salmochelin biosynthesis | Henderson et al. 2009, PLoS Pathog 5, e1000305 |

Deletion Strain Construction

In-frame deletions in UTI89 were made using the red recombinase method, as previously described, using pKD4 or pKD13 as a template. To confirm the appropriate deletions, PCR was performed with flanking primers. Antibiotic resistance insertions were removed by transforming the mutant strains with pCP20 expressing the FLP recombinase.

$^{13}$C and Deuterated Internal Standard Preparation $^{13}C_{21}$-yersiniabactin was produced by growing the siderophore overproducer UTI89Δfur as previously described. The isotope labeled supernatant was harvested by centrifugation and confirmed by LC-MS detection of $^{13}C_{21}$-ferric yersiniabactin at m/z 556 (FIG. 8). $^{13}C_{21}$-ferric yersiniabactin and $^{13}C_{21}$-cupric yersiniabactin were prepared by treating equal volumes of the labeled supernatant with 5 mM ferric chloride or 5 mM copper sulfate, respectively. Solutions were centrifuged in 15 mL falcon tubes at 6,000 rpm for 10 minutes. The supernatant from these metal treated samples was then subjected to preparative chromatography and eluted with 100% methanol. $d_4$-ferric-yersiniabactin was produced by chemically complementing the salicylate synthase-deficient mutant UTI89ΔybtS during growth in M63 minimal medium supplemented with 50 μM $d_6$-salicylate and 0.2% unlabeled glycerol. The isotope-labeled supernatant was harvested by centrifugation and confirmed by LC-MS detection of $d_4$-ferricyersiniabactin at m/z 539 (FIG. 9). The m/z 539 MS/MS product ion spectrum of this ion retained the 187 amu neutral loss as expected for deuterium incorporation in the yersiniabactin phenyl ring.

Yersiniabactin Purification

Apo-yersiniabactin was purified from UTI89ΔentB culture supernatants, which lack enterobactin or salmochelin. Metal complexes of yersiniabactin were generated by adding 1.0 M ferric chloride or copper sulfate to UTI89ΔentB cell culture supernatants to a final concentration of 5 mM. Metal-treated supernatants were incubated for 15 minutes at room temperature and centrifuged for 2 minutes at 14,000 rpm. The supernatant was then applied to a conditioned preparative reverse phase column (Waters Sep-Pak C18 cartridges), washed with 2 mL of 20% methanol and eluted with 1 mL of 80% methanol. A centrifugal evaporator was used to concentrate the eluate. Samples were resuspended in 20% methanol and further purified by high-performance liquid chromatography. Samples were applied to a Resource™ 1 mL RPC column (GE Healthcare). The gradient used was as follows: Solvent A (100% deionized water) was held constant at 98% and solvent B (100% methanol) was held constant at 2% for 2 minutes, followed by a linear gradient where solvent B was increased to 100% over 20 minutes and then held constant at 100% for 2 minutes. Eluted samples were subsequently concentrated in a centrifugal evaporator and resuspended in 100 μL deionized water. Following mass spectrometric confirmation, apo-yersiniabactin concentration was determined spectrophotometrically following conversion to ferric-yersiniabactin ($\epsilon_{385}$=2,884 $M^{-1}$ $cm^{-1}$) with 5 mM ferric chloride.

Liquid Chromatography-Mass Spectrometry

LC-MS analyses were conducted using a Shimadzu UFLC-equipped AB-Sciex 4000 QTrap operated in positive ion mode using the Turbo V ESI ion source and a Thermo LCQ Deca. The QTrap samples were injected onto a Fused-core phenylhexyl column (100×2 mm, 2.7 μm particle, Ascentis Express, Supelco) with a flow rate of 0.4 mL/min. The gradient used was as follows: Solvent A (0.1% formic acid) was held constant at 98% and solvent B (100% acetonitrile in 0.1% formic acid) was held constant at 2% for 2 minutes, solvent B was increased to 65% by 10 minutes and then to 98% by 12 minutes. The ion spray voltage was set to 5 kV. The heater temperature was 500° C. The declustering potential, nebulizer gas (G1), auxiliary gas (G2) and collision energy were set at 110, 40, 35 and 35V, respectively. In vivo Cu(II)-Ybt quantification was carried out in the MRM mode using $^{13}$C-labeled siderophore standards with previously identified CID fragmentations. Cu(II)-Ybt/Fe(III)-Ybt ratio determinations were made by calibrating with standard curves conducted in 1×PBS buffer for in vitro or human urine for in vivo determinations (FIG. 10).

Liquid Chromatography-Constant Neutral Loss (LC-CNL) Scan Analysis

The UFLC-4000 QTrap was used with the chromatography and ion source settings described above to identify compounds with a common neutral fragment loss of 187 m/z units. The collision energy was set to 35 V and the first mass analyzer (Q1) was set to scan from m/z 200 to 700 amu while the second mass analyzer (Q3) simultaneously scanned at 187 m/z units less than Q1. Sensitivity was maximized by selecting the low-resolution (2 mass unit window, 0.7 FWHH) setting. In this manner, only ions exhibiting a neutral loss of 187 mass units were detected. As $d_4$-ferric-yersiniabactin retained the 187 amu neutral loss, it was used as an internal standard in this analysis.

Human Specimen Collection

Study protocols were approved by the Institutional Review Board of the University of Washington. All patients provided written informed consent for the collection of samples and subsequent analysis. Clean-catch midstream urine specimens were obtained from female patients at the University of Washington, Seattle, Wash. with acute uncomplicated cystitis using previously described symptoms of dysuria, urinary frequency, or urinary urgency with a concentration of uropathogens in the urine of z 1×10$^2$ colony-forming units (CFU/mL). One-tenth volume of Sigma FAST protease inhibitor solution (Sigma, St. Louis, Mo.) was added to freshly voided urines prior to clinical centrifugation to remove cellular material and the supernatant was frozen at −80 C. Uropathogens in midstream urine were identified using standard methods. *E. coli*

UTI urine specimens and pathogen isolates with urine white blood cell count 350 collected between Jan. 6, 2010 and Nov. 15, 2010 were selected for analysis.

Mouse Infections

Six- to seven-week old female C3H/HeN mice obtained from Harlan Sprague Dawley, Inc. (Indianapolis, Ind.) were infected with $10^7$ CFU/mL UTI89 or PBS control as described. Murine urine samples were collected on the day of tissue harvest. Bladders were aseptically harvested at the indicated time point and homogenized in 1 mL PBS. CFU determination of viable bacteria in homogenates was conducted as described.

Biological Specimen Preparation

For the purposes of LC-CNL scans, urine samples from healthy volunteers were collected and pooled in metal-free Nalgene beakers and centrifuged in 50 mL Falcon flasks at 7,000 rpm for 15 minutes at 4° C. Apo-yersiniabactin and deuterated ferric-yersiniabactin internal standard were added to a final concentration of 20 μM to human urine supernatants to identify metal ion binding partners. To measure Cu(II)-Ybt in human urine, as well as murine urine and bladder homogenates, 2.5 μL each of $^{13}$C cupric- and ferric-internal standard was added to 850 μL of bladder homogenate or 500 μL urine, respectively. Samples were centrifuged at 14,000 rpm for 2 minutes. Yersiniabactin in the supernatant was extracted using preparative C18 chromatography (UCT, Inc., Bristol, Pa.) and eluted in 500 μL 100% methanol. Five microliters of the eluate was analyzed by LC-MS/MS to determine Cu(II)-Ybt levels.

Copper Mediated Cytotoxicity Assay

Following overnight growth in 50 mL M63 minimal media, bacterial cultures were washed twice in phosphate buffered saline (PBS, Sigma) and centrifuged at 6,500 rpm. Washed cultures were resuspended in fresh M63 minimal media, and normalized to $10^8$ CFU/mL for subsequent treatment. Normalized cultures were treated with varying concentrations of copper (II) sulfate and test agent in 2 mL reaction volumes in 6-well tissue culture plates. Samples were incubated for 20 hours at 37° C. with shaking. Bacterial viability was reported as the number of colony forming units per milliliter of the reaction volume post-treatment (CFU/mL).

Free Copper (I) Determinations

Free copper (I) was determined spectrophotometrically using the copper (I) indicator bathocuproine. Briefly, 25 μM bathocuproine, 25 μM apo-yersiniabactin, and 17.5 μM copper (II) sulfate, were used in combination in order-of-addition experiments, as well as alone as controls in PBS. Either 20 μM enterobactin (Sigma) or its catecholate moiety, 2,3-dihydroxybenzoic acid (DHB) were added as bioreductants. Following a 30 minute room temperature incubation, 25 μM bathocuproine was added and copper (I) levels were determined by measuring the visible absorbance at 480 nm of the cuprous-bathocuproine complex. Final concentrations of copper (I) were determined by comparison to a standard curve.

Determination of Cu(II)-Ybt to Fe(III)-Ybt Molar Ratios.

Cu(II)-Ybt to Fe(III)-Ybt molar ratios were determined using the calibration curves shown in FIG. 11.

Statistical Analyses

Statistics and graphs were generated using GraphPad Prism 4 (GraphPad Software, La Jolla, Calif.). For groupwise comparisons of siderophore production, the Mann-Whitney U Test was performed. The t-test was used to compare urinary versus rectal strain growth as well as growth differences between paired strains. Analyses of paired strain differences in siderophore production were performed using the Wilcoxon signed rank test for significance.

Introduction for Examples 11-15

Several functional studies have demonstrated that infection is accompanied by systemic changes in copper concentration within the host. Radiotracer studies with $^{64}$Cu have demonstrated that copper accumulates at sites of inflammation and within the exudates of wounds and burns where there exists an abundance of macrophages. Phagocytes such as macrophages represent one of the first lines of defense against invading microbial pathogens, and rely on high local concentrations of copper (II) for their bactericidal action. The debilitating effects of micromolar copper stress have been attributed to the de-regulation of iron homeostasis by the disruption of Fe≠S clusters in microbial proteins, as well as metal-catalyzed Fenton-type reactions. It is possible that by binding copper within the infection microenvironment, Cu(II)-Ybt complexes fulfill additional unappreciated biochemical roles that have important pathogenic consequences.

In the following examples, a new role for the Cu(II)-Ybt complex is established as a redox-active superoxide dismutase mimic that catalyzes the dismutation of superoxide anions. A physiologic context for this interaction is further established by demonstrating that the yersiniabactin-expressing uropathogen, UTI89, modulates the bactericidal activity of RAW264.7 macrophages. Structure-function experiments indicate that a direct interaction between salicylate and a redox-active metal is necessary to maintain the SOD activity of Cu(II)-Ybt compexes in the presence of protein. By time-dependent density-functional theory (TD-DFT) calculations, it is predicted that copper (II) is coordinated in a square planar configuration by contributions from four electron pairs from the yersiniabactin backbone. While cytoplasmic and periplasmic superoxide dismutases have been described in Enterobacteriaceae, this is the first report of a freely diffusible, virulence-associated extracellular SOD mimic. Together, these studies provide new insight into the molecular basis by which copper complexed yersiniabactin protects bacteria from host innate defenses.

Example 11

Increased Survival of Wild Type UTI89 in Response to Copper Challenge within RAW264.7 Macrophages To determine whether yersiniabactin modulates the copper-dependent bactericidal activity of macrophages, survival of the yersiniabactin deficient mutant UTI89 ΔybtS was compared to wild type control within RAW264.7 macrophages. RAW264.7 cells were incubated overnight in the presence or absence of 20 μM copper. Following overnight incubation, the macrophages were washed and infected with 1:10 cultures of UTI89 or ΔybtS, and bacterial survival was assessed by the number of colony forming units (CFU/mL) (FIGS. 12A and 12B). UTI89 exhibits significantly (approximately 2 log CFU/mL, p=0.001) greater number of viable colonies within copper treated RAW264.7 cells, compared to the ybtS deficient mutant. In contrast, survival of both UTI89 and the ΔybtS mutant was significantly (p=0.0032) reduced in RAW264.7 cells without copper treatment. The increase in survival of wild type UTI89 relative to the ybtS mutant occurs in a copper dependent manner, indicating that the wild type strain adapts to copper stress while the yersiniabactin deficient strain cannot. These findings support the hypothesis that yersiniabactin modulates the copper-dependent bactericidal activity of macrophages.

Example 12

Figure 13A:
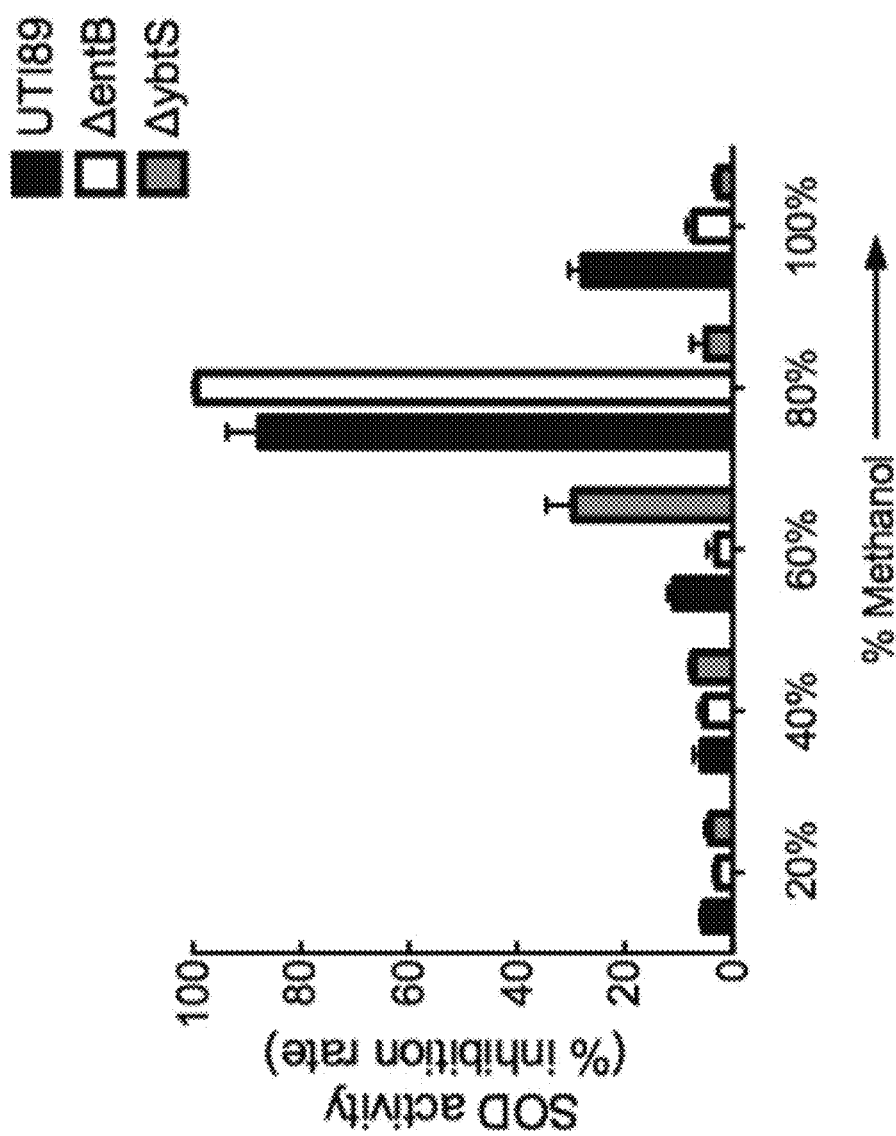
Figure 13B:
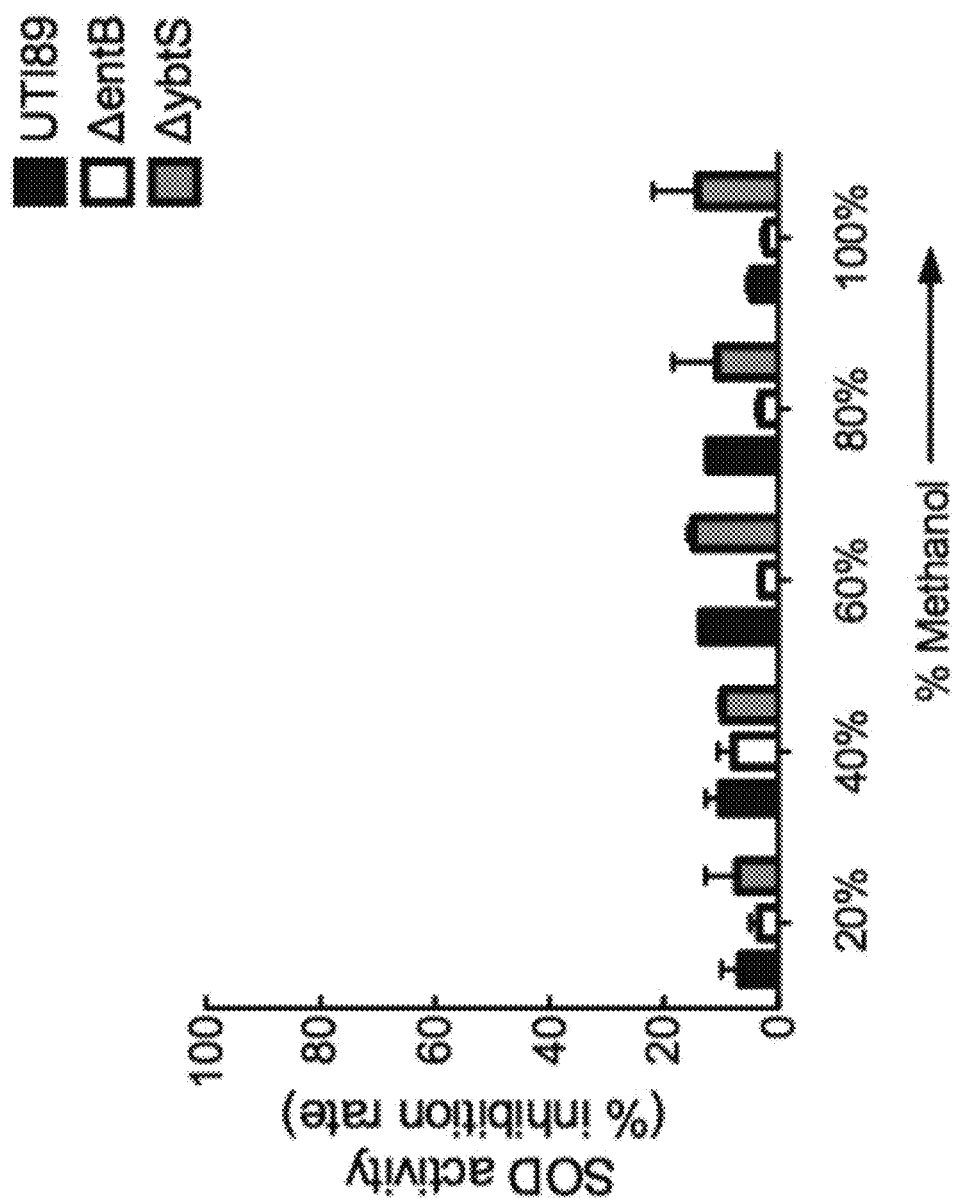

UTI89 Supernatant Reveals Superoxide Dismutase Activity in Fractions Associated with Yersiniabactin It has been demonstrated that superoxide radicals are the predominant oxygen-based radical species that are formed intracellularly by macrophages within the first 30-90 minutes immediately following phagocytosis. To determine whether cultures of UTI89 have the ability to selectively interact with superoxide species in a manner that leads to greater survival in macrophages, these cultures were tested for superoxide dismutase (SOD) activity. Cell cultures of UTI89, $\Delta$ybtS and $\Delta$entB (a siderophore mutant that overexpresses yersiniabactin) grown in M63 media were treated with or without 20 μM copper and crudely fractionated using preparative reverse-phase columns. Methanolic extracts were then dried, re-suspended in HPLC grade water and tested for SOD activity (FIGS. 13A and 13B). Copper-treated fractions of UTI89 and the entB deficient mutant demonstrated 87.6% and 99.4% SOD activity in the 80% crude methanolic extract normally associated with yersiniabactin purification. Only 24% superoxide activity was observed in the $\Delta$ybtS mutant in the 60% crude methanolic extract. Superoxide dismutase activity was not observed in any supernatants that were not treated with copper. To further confirm whether the SOD activity observed in the crude 80% extract from UTI89 and the entB mutant can be attributed directly to the presence of cupric-yersiniabactin, the crude extracts were purified and concentrated by HPLC. The greatest degree of SOD activity was concentrated in the 80% methanolic extract from UTI89 and $\Delta$entB supernatants (86.5% and 98.3%, respectively). These samples were confirmed as 99% pure cupric-yersiniabactin by LC-MS/MS.

Example 13

Cupric-Yersiniabactin is a Superoxide Dismutase Mimic

Copper chelation by yersiniabactin has been previously established (see Examples above). Additionally, precedent for superoxide dismutase activity in copper chelators has been established in certain environmental isolates. Superoxide dismutase activity attributed to copper (II)-yersiniabactin was determined directly by means of a xanthine/xanthine oxidase reaction system. In this WST-formazan-based assay, bovine Cu/Zn SOD dismutase completely inhibited superoxide anion formation. The SOD activity of cupric-yersiniabactin, calculated as a percentage inhibition rate, was 63.1% (FIG. 14A). In this system, copper sulfate alone demonstrated an inhibition rate of 33.8%, while apo-yersiniabactin alone did not demonstrate superoxide dismutase activity. To determine whether this phenotype is specific to the redox state of the metal bound to yersiniabactin, iron- and gallium-complexed yersiniabactin samples were generated in similar fashion (FIGS. 14B and 14C). While iron-complexed yersiniabactin complexes demonstrated SOD-like activity, the yersiniabactin complexed with redox inert gallium had an average optical density of 0.782 similar to the negative control, indicating that this activity was specific to the redox state of the metal. Notably, copper sulfate, ferric chloride, gallium nitrate, and apo-yersiniabactin did not demonstrate any superoxide dismutase like activity by themselves. Therefore, the superoxide dismutase activity can be attributed directly to non-inert metal-complexed siderophore itself.

The kinetics of this enzymatic activity were also determined with purified cupric-yersiniabactin complexes (FIG. 14D). For 0.12 mM, 0.6 mM, 3.0 mM and 15.0 mM solutions of cupric-yersiniabactin, the percentage inhibition rates were determined to be 4.6%, 19.8%, 24.3%, and 55.7%, respectively. In order to determine the complex concentration required yielding a 50% ($IC_{50}$) inhibition of the reaction, percentage of inhibition as a function of the logarithm of the metal-complexed siderophore concentration was plotted. These data indicate that cupric-yersiniabactin is a superoxide dismutase mimic, and that the rate of SOD activity is dose dependent.

Example 14

Yersiniabactin Retains Superoxide Dismutase Activity in the Presence of Albumin Copper (II) and copper (II)-salicylate complexes demonstrate superoxide dismutase activity, which can be quenched in the presence of low millimolar concentrations of serum albumin. To determine if yersiniabactin retains selective chemical advantage in a physiologic context, the superoxide dismutase activity of cupric-yersiniabactin was determined in the presence of 1.0 mg/mL bovine serum albumin. As previously described, serum albumin suppressed the catalytic activity of copper (II) and that of copper (II)-salicylate complexes, but had no effect on the catalytic activity of the cupric-yersiniabactin complex (FIGS. 15A and 15B). The ability of cupric-yersiniabactin to retain catalytic activity in the presence of albumin indicates that that complex is chemically stable in a biological environment, and thus provides a chemical rationale for its catalytic activity.

Example 15

Figure 16C:
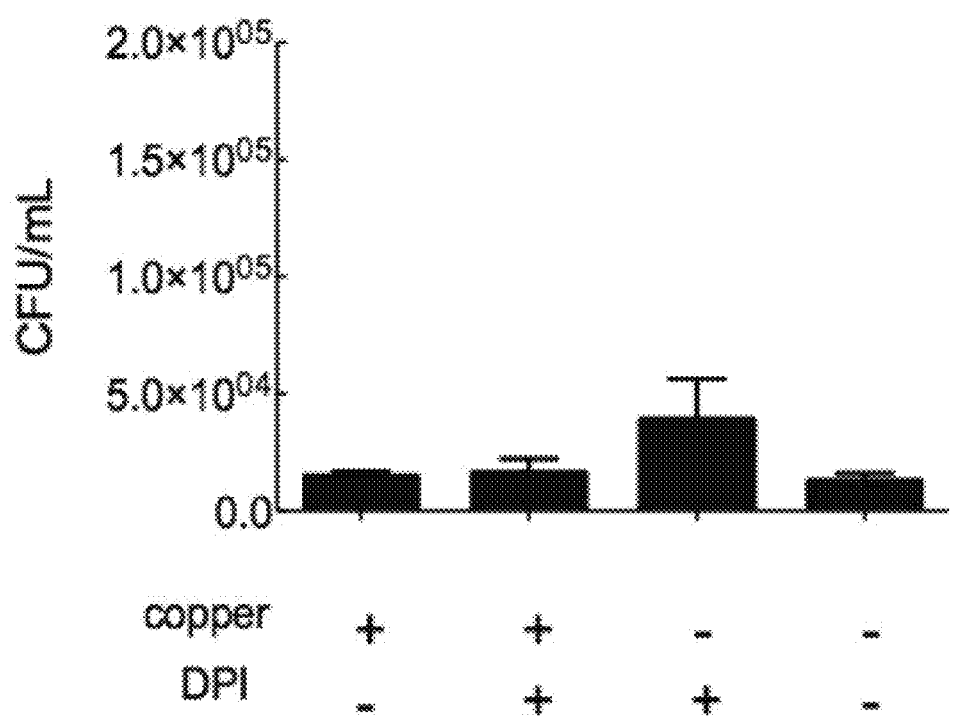

The Survival Phenotype Relies Upon Innate Production of Oxygen-Dependent Radicals by Macrophages To determine whether the yersiniabactin-mediated protection inside copper-treated macrophages relies on an interaction between cupric-yersiniabactin complexes with superoxide species in macrophages, ROS production by the NADPH oxidase complex was blocked by using 25 mM DPI (FIGS. 16A, 16B, and 16C). As expected, cells treated with DPI decreased oxidative-burst activity to background levels without any gross defect in phagocytosis (data not shown). Macrophages treated with neither DPI nor copper demonstrate a baseline bactericidal activity for both UTI89 and $\Delta$ybtS. A selective increase in the survival of UTI89 occurs only in macrophages treated with copper. Furthermore, comparison of these strains to a K12 strain, MG1655, indicates that the cytoprotective phenotype in copper-treated macrophages is specific to the strain expressing yersiniabactin. Treatment of macrophages with both copper and DPI, or with DPI alone results in reduced survival of wild-type bacteria to the same levels as MG1655 and the $\Delta$ybtS deficient mutant, abolishing the selective survival of wild-type cells observed in copper-treated macrophages. These findings indicate that DPI inhibition of the production of superoxide radicals by macrophages leads to a loss of the growth phenotype that is selectively observed in copper-treated macrophages. This suggests that copper(II)-yersiniabactin selectively interacts with, and dismutates superoxide anion in macrophages in vitro (FIG. 17).

Example 16

Figure 18A:
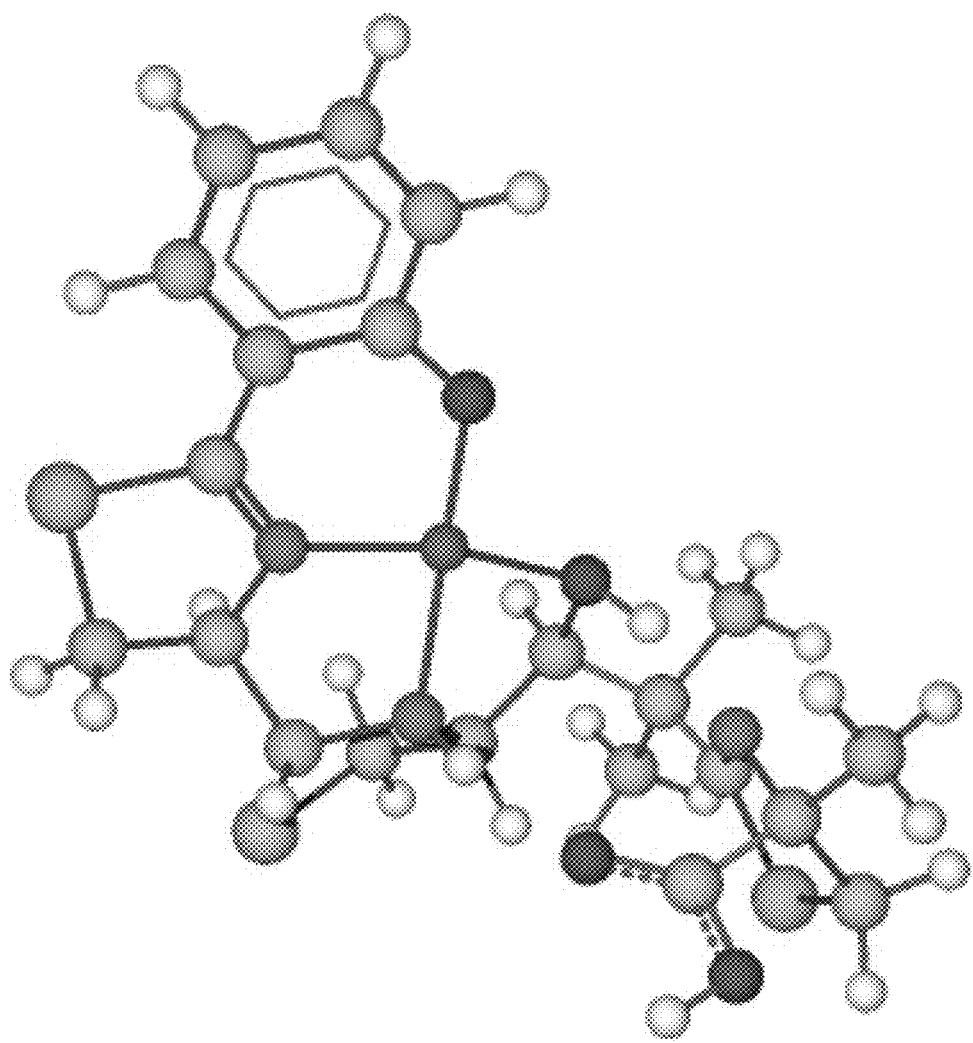

The Salicylate Moiety of Yersiniabactin Directly Contacts Copper (II) within Complex To determine which structural moieties of yersiniabactin contact copper (II) within the small molecule complex, density functional theory-based (DFT) simulations was employed, validated by CID fragmentation analysis of the ESI-generated positive ion. Previous crystallographic work indicates that yersiniabactin coordinates iron in an octahedral coordination by donation of six electron pairs: three from negatively charged oxygens of the phenolate, the ionized secondary alcohol, and the carboxylate and three from the neutral nitrogen atoms of the rings. As a control, our DFT approach yielded connectivity and structure of a neutral high-spin ferric complex essentially identical to the crystallographic structure. Similar structures were maintained for both the anionic and cationic form of the ferric complex achieved by subtraction or addition of a proton, respectively. In contrast, the DFT simulation of the copper(II)-yersiniabactin complex in both neutral and cationic form supports square-planar coordination of the cupric atom by the phenolate and secondary alcohol oxygens and two sets of electron pairs from the neutral nitrogen atoms, as the most stable cupric yersiniabactin structure (FIG. 18A).

Unlike the compact ferric complex, the cupric complex has a free arm consisting of the terminal ring and carboxylate, in effect, loss of 187 amu is already pre-loaded.

Figure 18B:
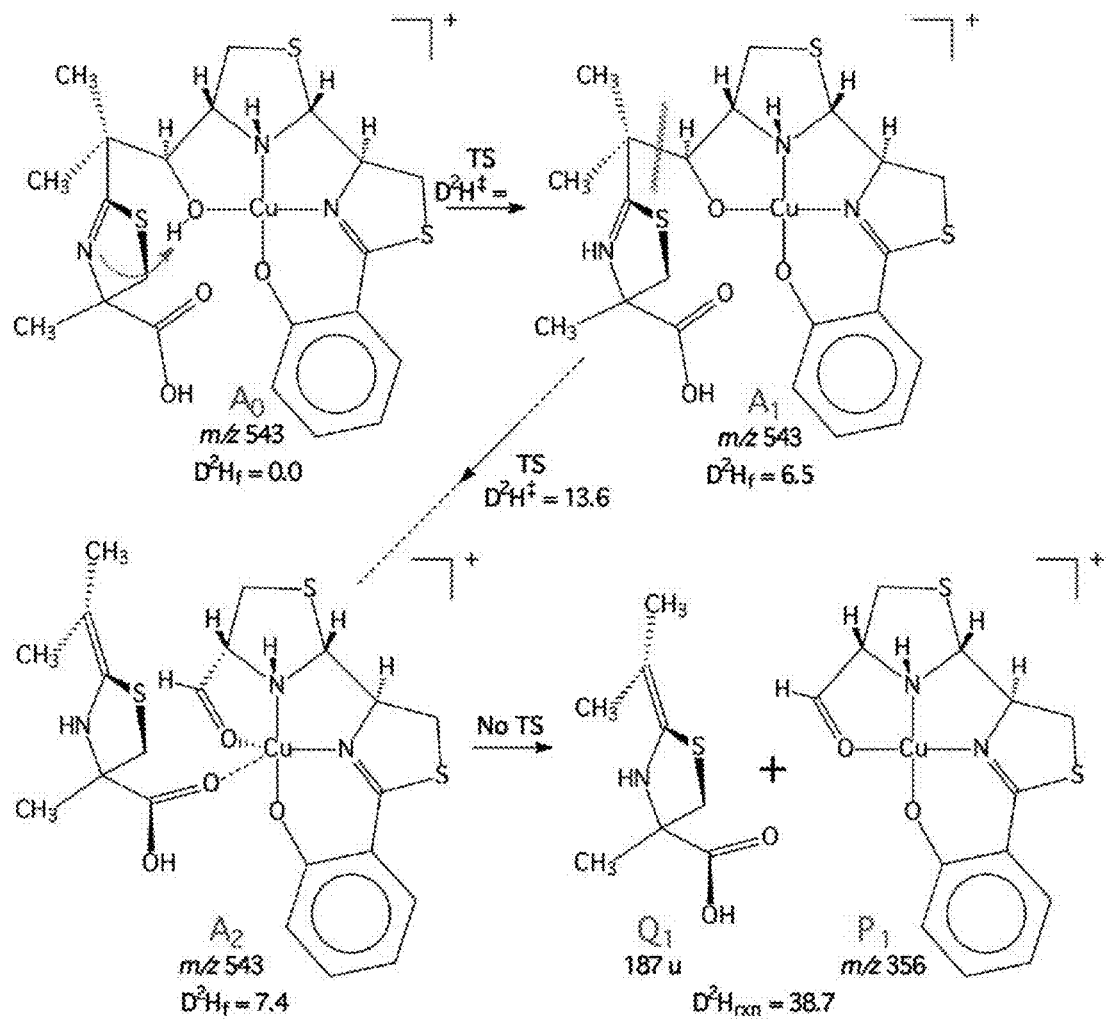

Experimental validation of this model was provided by CID fragmentation analysis of ESI-generated cations. The MS/MS ion spectra of m/z 543 from peak 1 is dominated by the predicted neutral loss of 187 amu (FIG. 18B). An additional fragment at m/z 328 is also observed. MS/MS of the $^{65}$Cu isotopomer revealed a similar fragmentation pattern shifted upward by 2, consistent with the copper-containing CID fragments. The favorable loss of 187 mass units was consistent with DFT calculations of this complex, which predict carbon-carbon bond cleavage through a modest barrier of 13.7 kcal/mol relative to most stable form $A_0$ followed by separation of the copper-bonded fragment and the 187 amu moiety which requires 38.7 kcal/mol relative to $A_0$. The resultant aldehydic moeity in the intermediate product ion is consistent with the observed CO (28 amu) loss. Together these data provide a structural rationale supporting yersiniabactin as a facile copper ligand in which the cupric ion is coordinated directly to the phenolate oxygen.

Discussion for Examples 11 to 16

The results presented above demonstrate that yersiniabactin expression protects uropathogenic E. coli from macrophage respiratory burst. A new function for the virulence-associated siderophore yersiniabactin as a copper (II)-dependent superoxide dismutase mimic was determined. Additionally the structure-activity relationship between yersiniabactin and copper (II) was analyzed to establish a chemical rationale for the biosynthetic expense associated with the expression of multiple siderophore types by Enterobacteriaceae. By conducting density functional theory-based (DFT) simulations, the structural moieties of yersiniabactin that contact copper (II) within the small molecule complex were determined.

Secreted copper chelators have been previously described among multiple environmental bacterial isolates. In this context, yersiniabactin is a virulence-associated functional homologue of methanobactin, a chromopeptide whose complexes with copper demonstrate superoxide dismutase, oxidase and hydrogen peroxide reductase properties. The SOD activity associated with copper (II)-yersiniabactin complexes is of particular importance given that the uptake of copper (II) is recognized to be of critical importance in the interaction between macrophages and intracellular pathogens. The ability of yersiniabactin to neutralize host defenses by binding copper (II) and the additional property of this complex to dismutate superoxide radicals, therefore, has physiological relevance as both activities may contribute to the relative success of E. coli to colonize a particular host niche persistently.

Reaction mechanisms of copper-complexed aromatic compounds exhibiting SOD activity suggest that superoxide anions react primarily with the copper (II) held within the copper (II)-yersiniabactin complex, rather than the yersiniabactin backbone (1, 2).

$$Cu(II)+O_2\bullet^- \rightarrow Cu(I)+O_2 \quad (1)$$

$$O_2\bullet^- + Cu(I) + 2H^+ \rightarrow Cu(II) + H_2O_2 \quad (2)$$

The reaction with superoxide anion reduces copper (II) to copper (I), which in turn gets oxidized by interaction with another superoxide anion, releasing molecular oxygen and thereby regenerating the parent copper (II)-complex. Initial DFT simulations suggest that direct interaction of superoxide anion with copper (II) in complex with yersiniabactin is energetically favorable (FIG. 19). Therefore, the catalytic activity is mainly a result of the reversible redox reactions within the Cu(II)/Cu(I) couple in the complex. Alternatively, excess superoxide anions may oxidize the phenolic moiety of yersiniabactin, resulting in the transient formation of phenoxyl radicals. These phenoxyl radicals may react with reduced copper ions of the complex and also result in regeneration of the complex.

Nonribosomal polyketide synthase assembly lines yield remarkably complex chemical scaffolds fashioned from simple building blocks such as acyl-CoAs and amino acids, achieving high functional group density and molecular diversity. The synthesis of multiple complex natural products such as siderophores with redundant function is intriguing from an evolutionary perspective. It has been argued that unlike primary metabolic pathways, secondary metabolic products are promiscuous and favor molecular diversity. The tendency of microbial secondary pathways to produce a suite of natural products with molecular diversity may additionally result from selective pressure within host niches. Yersiniabactin's ability to bind copper and the structure-activity relationship that informs this activity may thus reflect an example of microbial convergent chemical evolution in response to selective host pressures. Similarly, other microbial siderophores and natural microbial products may facilitate additional enzymatic or catalytic functions that have been previously unappreciated. With greater understanding of the microbial secondary product structures and their biosynthetic pathways, we may be able to integrate their biochemical and physiological roles in a broader evolutionary perspective.

Materials and Methods for Examples 11-16

Bacterial Strains and Cultivation

UTI89, a well characterized and fully sequenced uropathogenic E. coli strain, was used as the prototypic pathogen in these examples. UTI89 mutant strains are listed in Table 2. Bacterial cultures were grown from a single colony in Difco™ Luria-Bertani broth, Miller (LB) (BD, Franklin Lakes, N.J.) for three hours, and subsequently diluted 1:100 into M63 medium supplemented with 0.2% glycerol and 10 mg/mL niacin (Sigma). Bacterial cultures were incubated for 18 hours at 37° C. in a rotary shaker.

TABLE 2

UTI89 mutant strains used in this study.

| Strain | Gene function | Reference |
| --- | --- | --- |
| UTI89ΔybtS | salicylate synthase, yersiniabactin biosynthesis | Snyder et al. 2004. Infect Immun 72: 6373-6381 |
| UTI89ΔentB | isochorismate lyase, catecholate siderophore (enterobactin/salmochelin) biosynthesis | Snyder et al. 2004. Infect Immun 72: 6373-6381 |

Deletion-Strain Construction

In-frame deletions in UTI89 were made using the red recombinase method, as previously described, using pKD4 or pKD13 as a template. To confirm the appropriate deletions, PCR with flanking primers was performed. Antibiotic resistance insertions were removed by transforming the mutant strains with pCP20 expressing the FLP recombinase.

Chemicals and Reagents

Methanol (HPLC grade) and water (HPLC grade) were purchased from Fisher Scientific (Fisher Scientific, Pittsburg, Pa., USA). Salicylic acid, cupric sulfate, ferric chloride, gallium nitrate, and bovine serum albumin were purchased from Sigma (Sigma-Aldrich Corporation, Saint Louis, Mo., USA).

Tissue Culture

RAW264.7 cells were obtained from the American Type Culture Collection (Manassas, Va.) and maintained in Gibco's RPMI 1640 medium (Invitrogen) containing 10% fetal bovine serum in 5% $CO_2$ at 37° C.

Bacterial Survival within RAW 264.7 Macrophages

RAW264.7 macrophages were detached from TPP cell culture flasks by scraping into ice-cold medium containing 10% FBS, washed twice, and resuspended in triplicate in 24-well plates at $10^5$ cells/well. The seeded wells were treated in the following order: 24 hours in i) ice cold media containing 10% FBS, followed by a 24 hour incubation in ii) serum-free media, followed by a 24 hour incubation iii) in serum-free media either with or without 20 μM $CuSO_4$. Wild type *E. coli* (strain UTI89), ΔybtS, or MG1655 were grown for 18 hours to stationary phase in M63 minimal media and added to the RAW264.7 macrophages at a macrophage/bacteria ratio of 1:10 or 1:1. Bacterial phagocytosis was allowed to proceed for 30 min at 37° C. At 30 minutes, one set of samples (total inoculum) was lysed in 0.1% Triton X-100 solution and plated onto LB-agar plates for CFU enumeration to provide total bacterial inoculum. A second set (adherent group) was washed 4 times with 1× ice-cold PBS to wash extracellular bacteria, lysed with serum-free media containing 0.1% Triton X-100 and plated as described above. A third set of samples (kill group) was treated with serum-free media containing 100 g/ml gentamicin (Invitrogen), and incubated for one hour to allow bacterial killing to occur in the RAW264.7 cells. Following this incubation period, the samples were washed 4 times with 1×PBS to remove extracellular gentamycin, and then lysed with 0.1% Triton, and plated onto LB-agar. Bacterial survival was determined as the ratio of CFU in the killing group over CFU of the uptake group.

Inhibition of Oxygen Dependent Innate Activity of RAW264.7 Cells

Diphenyleneiodonium (DPI) produces a non-competitive inhibition of NADPH oxidase by its covalent binding to FAD. RAW264.7 macrophages were infected with bacteria as described above, and samples were treated with 20 μM DPI (Sigma) inhibitor. Samples containing media alone, media with 20 μM copper, or media with both 20 μM and 10 μM DPI were used as additional controls.

Superoxide Dismutase Activity

Superoxide dismutase (SOD) activity was measured indirectly in multiwell plates, using xanthine/xanthine oxidase as the superoxide-generating system and the reduction of Dojindo's highly water-soluble tetrazolium salt, WST-1 (2-(4-Iodophenyl)-3-(4-nitrophenyl)-5-(2,4-disulfophenyl)-2H-tetrazolium, monosodium salt) to produce a water-soluble formazan dye as the detector (Sigma-19160). Reduction of WST-1 was monitored at 440 nm in a final volume of 100 μL. One unit of activity was defined as the amount of compound which blocked 50% WST-1 reduction under these conditions. Bovine Cu/Zn SOD was used as a standard (Sigma S-7571). Controls for the SOD assay included ensuring that the compound did not affect the superoxide-generating reaction, testing solvent alone, and ensuring that the compound does not react independently with WST-1. To determine whether SOD activity is retained in the presence of protein, these experiments were repeated in the presence of 1.0 mg/mL bovine serum albumin (Sigma).

Yersiniabactin Isolation and Characterization 1.0 M ferric chloride or copper sulfate was added to UTI89ΔentB cell culture supernatants to a final concentration of 50 mM and purified as described previously. The supernatant from this precipitation reaction was harvested by centrifugation and subsequently subjected to preparative chromatography, and eluted with 100% methanol. The presence of cupric and ferric yersiniabactin was confirmed by LC-MS detection of these complexes at m/z 543 and 535, respectively.

High Resolution Liquid Chromatography-Mass Spectrometry

High resolution mass spectrometry analyses of cupric- and ferric-yersiniabactin complexes were conducted using a Bruker Maxis Q-T of operated in positive ion mode as previously described. The samples were directly infused at a flow rate of 0.3 μL/min. The ion spray voltage was set to 4500 V for positive ion and −500 V for negative ion mode, respectively. The nebulizer gas (air) and turbo gas (air) were set to 0.4 bar and 4.0 L/min, respectively. The heater temperature was 180° C.

Theoretical Calculations

Theoretical calculations were performed to characterize the potential-energy surface (PES) associated with fragmentation. Conformer spaces for precursors (cupric and ferric complexes with yersiniabactin) and intermediates were explored by Monte-Carlo/MMFF molecular mechanisms/dynamics methods. From these results, structures of precursors, intermediates, and scans for associated transition states were explored by using the PM3 semi-empirical algorithm, both in Spartan for Linux v. 2 (Wavefunction, Inc.). Minima and transition states were optimized by DFT (Density Function Theory, part of Gaussian 03 suite, Gaussian Inc.) with functional PBE0 (PBE1PBE in Gaussian parlance) with basis set Def2-SVP confirmed by vibrational frequency analysis. In addition, connections of transition states to minima were examined by inspection, projections along normal reaction coordinates, and path calculations as necessary. Single-point energies were calculated at level PBE1 PBE/Def2-SVP and scaled thermal-energy corrections were applied using scaling factors for B3LYP/6-31G(d,p). The hybrid functional and basis sets were chosen on basis performance with transition metal complexes. DFT was selected for high-level calculations because it requires less computational overhead than ab initio methods and performs adequately. All results are reported in kJ/mol as enthalpies of formation relative to a selected, suitable precursor.

The complexes are all radicals because of the transition-metal cation involved. The cupric complexes are spin 1/2 with the $Cu^{2+}$ in low-spin state whereas the ferric complexes have spin 5/2 with the $Fe^{3+}$ in high-spin state.

Statistical Analyses

Statistics and graphs were generated using GraphPad Prism 4. The t test was used to compare growth differences between paired strains. Analyses of paired strain differences in siderophore production were performed using the Wilcoxon signed rank test for significance.

Example 17

Small Molecule Inhibitor of Yersiniabactin Biosynthesis

Para-aminosalicylic acid (PAS, 4-aminosalicylate) is an early antituberculosis drug identified and used in the 1940's. It is currently used rarely for highly drug resistant tuberculosis infections. While PAS's primary mechanism of action has been historically considered to be inhibition of para-aminobenzoic acid (PABA) biosynthesis, comparable to sulfa drugs, recent work (FEMS Microbial Lett. 2010 oct; 311(2): 193-9.) suggests that it is capable of inhibiting mycobactin biosynthesis in mycobacteria. Mycobactin is a siderophore believed to be important for *Mycobacterium tuberculosis* infections.

The Examples above suggest that the siderophore yersiniabactin is an important virulence factor in urinary pathogenic *E. coli*. The ability of PAS to inhibit yersiniabactin biosynthesis in a urinary pathogenic *E. coli* strain was examined. PAS was observed to selectively inhibit yersiniabactin biosynthesis at levels where it did not inhibit in vitro growth.

The relatively low toxicity of PAS makes possible a quick translation to evaluation in animal models and humans. In UTI, *E. coli* cystitis strains that progress to bacteremia and sepsis carry a genetic marker of yersiniabactin production at high frequency.

What is claimed is:

1. A method for detecting the presence of yersiniabactin-expressing bacteria in a subject, the method comprising the steps of:
    a) obtaining a sample from the subject,
    b) analyzing the sample, in vitro, by mass spectrometry for the presence or absence of cupric yersiniabactin, wherein the detection of a peak with m/z 543 detects cupric yersiniabactin, and
    c) identifying the presence of yersiniabactin-expressing bacteria in the subject when cupric yersiniabactin is present in the sample.

2. The method of claim 1, wherein the sample is a urine sample.

3. The method of claim 1, wherein the yersiniabactin-expressing bacteria is uropathogenic bacteria.

4. The method of claim 1, wherein the yersiniabactin-expressing bacteria is uropathogenic *E. coli*.

5. The method of claim 1, wherein the sample is analyzed using liquid chromatography.

6. The method of claim 1, wherein the sample is a urine sample, and the yersiniabactin-expressing bacteria are uropathogenic bacteria.

7. The method of claim 1, wherein the subject has recurrent urinary tract infections.

8. The method of claim 1, wherein the detection of a second peak with m/z 545 detects cupric yersiniabactin.

* * * * *